United States Patent
Prossnitz et al.

(10) Patent No.: US 10,980,785 B2
(45) Date of Patent: *Apr. 20, 2021

(54) METHOD FOR TREATING OBESITY, DIABETES, CARDIOVASCULAR AND KIDNEY DISEASES BY REGULATING GPR30/GPER ACTIVITY

(71) Applicant: UNM Rainforest Innovations, Albuquerque, NM (US)

(72) Inventors: Eric R. Prossnitz, Albuquerque, NM (US); Geetanjali Sharma, Albuquerque, NM (US); Matthias Barton, Zurich (CH); Matthias R. Meyer, Stallikon (CH)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/577,661

(22) Filed: Sep. 20, 2019

(65) Prior Publication Data
US 2020/0113875 A1 Apr. 16, 2020

Related U.S. Application Data

(60) Continuation of application No. 16/033,008, filed on Jul. 11, 2018, now Pat. No. 10,471,047, which is a division of application No. 15/556,055, filed as application No. PCT/US2016/020452 on Mar. 2, 2016, now Pat. No. 10,251,870.

(60) Provisional application No. 62/129,224, filed on Mar. 6, 2015, provisional application No. 62/136,820, filed on Mar. 23, 2015, provisional application No. 62/217,434, filed on Sep. 11, 2015.

(51) Int. Cl.
| | | |
|---|---|---|
| A61K 31/436 | (2006.01) | |
| A61K 31/435 | (2006.01) | |
| A61K 31/4355 | (2006.01) | |
| A61K 31/437 | (2006.01) | |
| A61K 31/16 | (2006.01) | |
| A61K 31/7088 | (2006.01) | |
| A61K 38/28 | (2006.01) | |

(52) U.S. Cl.
CPC .......... *A61K 31/436* (2013.01); *A61K 31/16* (2013.01); *A61K 31/435* (2013.01); *A61K 31/437* (2013.01); *A61K 31/4355* (2013.01); *A61K 31/7088* (2013.01); *A61K 38/28* (2013.01); *G01N 2800/042* (2013.01)

(58) Field of Classification Search
None
See application file for complete search history.

(56) References Cited

U.S. PATENT DOCUMENTS

| | | |
|---|---|---|
| 6,265,147 B1 | 7/2001 | Mobley et al. |
| 7,875,721 B2 | 1/2011 | Prossnitz et al. |
| 8,487,100 B2 | 7/2013 | Prossnitz et al. |
| 10,251,870 B2 | 4/2019 | Prossnitz et al. |
| 10,471,047 B2 | 11/2019 | Prossnitz et al. |
| 10,682,341 B2 | 6/2020 | Prossnitz et al. |

FOREIGN PATENT DOCUMENTS

WO 2013102929 A1 7/2013

OTHER PUBLICATIONS

Lassegue B, et al. Biochemistry, physiology, and pathophysiology of nadph oxidases in the cardiovascular system. Circ Res. 2012;110:1364-1390.
Lakatta EG. Arterial and cardiac aging: Major shareholders in cardiovascular disease enterprises: Part iii: Cellular and molecular clues to heart and arterial aging. Circulation. 2003;107:490-497.
Suh YA, et al. Cell transformation by the superoxide-generating oxidase mox1. Nature. 1999;401:79-82.
Lassegue B, et al. Novel gp91(phox) homologues in vascular smooth muscle cells: Nox1 mediates angiotensin II-induced superoxide formation and redox-sensitive signaling pathways. Circ Res. 2001;88:888-894.
Wingler K, et al. Upregulation of the vascular nad(p)h-oxidase isoforms nox1 and nox4 by the renin-angiotensin system in vitro and in vivo. Free Radic Biol Med. 2001;31:1456-1464.
Nguyen D, et al. Angiotensin II, nadph oxidase, and redox signaling in the vasculature. Antioxid Redox Signal. 2013;19:1110-1120.
Gavazzi G, et al. Decreased blood pressure in nox1-deficient mice. FEBS Lett. 2006;580:497-504.
Matsuno K, et al. Nox1 is involved in angiotensin II-mediated hypertension: A study in nox1-deficient mice. Circulation. 2005;112:2677-2685.
Dikalova A, et al. Nox1 overexpression potentiates angiotensin II-induced hypertension and vascular smooth muscle hypertrophy in transgenic mice. Circulation. 2005;112:2668-2676.
Mori T, et al. Enhanced cardiac inflammation and fibrosis in ovariectomized hypertensive rats: A possible mechanism of diastolic dysfunction in postmenopausal women. Hypertens Res. 2011;34:496-502.
Revankar CM, et al. A transmembrane intracellular estrogen receptor mediates rapid cell signaling. Science. 2005;307:1625-1630.
Isensee J, et al. Expression pattern of G protein-coupled receptor 30 in lacz reporter mice. Endocrinology. 2009;150:1722-1730.

(Continued)

*Primary Examiner* — Heidi Reese
(74) *Attorney, Agent, or Firm* — Henry D. Coleman; R. Neil Sudol

(57) ABSTRACT

The current invention is in the field of molecular biology/pharmacology and provides methods of using compounds that modulate the effects of GPR30/GPER for treating obesity and diabetes (preferably agonists) as well as disease states and/or conditions that result from excessive formation of reactive oxygen species (preferably antagonists). These compounds may function as agonists and/or antagonists of the disclosed estrogen receptor and/or modulate the expression/upregulation of nox and nox-associated reactive oxygen species (ROS).

3 Claims, 35 Drawing Sheets

(56) References Cited

OTHER PUBLICATIONS

Meyer MR, et al. Deletion of G protein-coupled estrogen receptor increases endothelial vasoconstriction. Hypertension. 2012;59:507-512.

Haas E, et al. Regulatory role of G protein-coupled estrogen receptor for vascular function and obesity. Circ Res. 2009;104:288-291.

Lindsey SH, et al. Chronic treatment with the G protein-coupled receptor 30 agonist G-1 decreases blood pressure in ovariectomized mRen2.Lewis rats. Endocrinology. 2009;150:3753-3758.

Rey FE, et al. Novel competitive inhibitor of nad(p)h oxidase assembly attenuates vascular o(2)(−) and systolic blood pressure in mice. Circ Res. 2001;89:408-414.

Dai DF, et al. Cardiac aging: From molecular mechanisms to significance in human health and disease. Antioxid Redox Signal. 2012;16:1492-1526.

Boyle AJ, et al. Cardiomyopathy of aging in the mammalian heart is characterized by myocardial hypertrophy, fibrosis and a predisposition towards cardiomyocyte apoptosis and autophagy. Exp Gerontol. 2011;46:549-559.

Ram R, et al. New approaches in small animal echocardiography: Imaging the sounds of silence. Am J Physiol Heart Circ Physiol. 2011;301:H1765-1780.

Griendling KK, et al. Angiotensin II stimulates nadh and nadph oxidase activity in cultured vascular smooth muscle cells. Circ Res. 1994;74:1141-1148.

Guerra AN, et al. Nucleotide receptor signalling and the generation of reactive oxygen species. Purinergic Signal. 2007;3:39-51.

Dennis MK, et al. Identification of a GPER/GPR30 antagonist with improved estrogen receptor counterselectivity. J Steroid Biochem Mol Biol. 2011;127:358-366.

Prossnitz ER, Barton M. The G-protein-coupled estrogen receptor GPER in health and disease. Nat Rev Endocrinol, 2011;7:715-726.

Mauvais-Jarvis F. Estrogen and androgen receptors: regulators of fuel homeostasis and emerging targets for diabetes and obesity. Trends in Endocrinology and Metabolism, 2011;22:24-33.

Kumar R, et al. Endocrinology, 2011;152:2568-2579.

Sharma G, et al. GPER deficiency in male mice results in insulin resistance dyslipidemia, and a proinflammatory state. Endocrinology, 2013;154(11):4136-4145.

Burai R, et al. Highly efficient synthesis and characterization of the GPR30-selective agonist G-1 and related tetrahydroquinoline analogs. Org Biomol Chem, 2010; DOI: 10.1039/c001307b.

Dennis MK, et al. Identification of GPER/GPR30 antagonist with improved estrogen receptor counterselectivity. J Steroid Biochem Mol Biol, 2011;127(3-5):358-366.

Filardo EJ, et al. Minireview: G protein-coupled estrogen receptor-1, GPER-1: its mechanism of action and role in female reproductive cancer, renal and vascular physiology. Endocrinology, 2012;153(7):2953-2962.

GPER-selective agonist G-1 attenuates adiposity
in male and female models of obesity/diabetes A: Females B: Males G-1 treatment increases energy expenditure in obese male and female mice

A: Females

B: Males

G-1 improves glucose tolerance and reduces fasting glucose in obese/diabetic female mice

A: Females

G-1 improves glucose tolerance, insulin sensitivity and reduces fasting glucose
in obese/diabetic male mice

B: Males

G-1 treatment reduces visceral adiposity in female obese mice

G-1 treatment reduces visceral adiposity in male obese mice

G-1 treatment decreases expression of inflammatory, angiogenic and lipogenic markers in gonadal fat of obese female mice G-1 treatment decreases expression of inflammatory and lipogenic markers in multiple tissues of female mice G-1 treatment reduces lipid accumulation and adipogenesis markers in adipocytes G-1 treatment increases glucose uptake in differentiated myocytes G-1 activates AMPK and increases mitochondrial biogenesis in murine 3T3-L1 cells Fig. 20
Table 1

| | $Gper^{+/+}$ | $Gper^{-/-}$ | P value |
|---|---|---|---|
| IVS end-diastolic (mm) | 1.5±0.1 | 1.0±0.1 | 0.01 |
| PW end-diastolic (mm) | 1.8±0.1 | 1.1±0.2 | 0.04 |
| LVEDD (mm) | 3.4±0.1 | 3.8±0.3 | ns |
| LVESD (mm) | 1.9±0.0 | 2.6±0.3 | ns |
| LV mass (mg) | 201±23 | 117±11 | 0.03 |
| Relative wall thickness | 1.0±0.1 | 0.5±0.1 | 0.04 |
| EF (%) | 45±4 | 46±2 | ns |
| E/A ratio | 1.2±0.2 | 1.6±0.0 | ns |
| Heart rate (bpm) | 382±26 | 394±18 | ns |
| Systolic blood pressure (mmHg) | 121±2 | 119±1 | ns |
| Diastolic blood pressure (mmHg) | 89±2 | 90±1 | ns |

Fig. 21

Animal Characteristics

| | 4 month-old | | 12 month-old | | 24 month-old | |
|---|---|---|---|---|---|---|
| | WT | KO | WT | KO | WT | KO |
| Body Weight, g (n) | 27.3±0.5 (13) | 29.5±1.9 (5) | 36.4±1.2 (21) | 41.3±1.2 (19)**,† | 30.8±1.1 (7) | 34.4±2.0 (8) |
| Tibial Length, mm (n) | - | - | 18.7±0.1 (21) | 18.6±0.1 (18) | 18.2±0.1 (7) | 18.3±0.1 (7) |
| Kidney Weight, mg (n) | 168±5 (8) | 175±11 (5) | 236±13 *(11) | 256±7 *(10) | 554±94 *(7) | 306±11 (8)*,† |
| Kidney/BW, mg/g (n) | 6.1±0.2 (8) | 6.0±0.2 (5) | 6.7±0.4 (11) | 6.4±0.2 (10) | 18.3±3 *(7) | 9.1±0.5 (8)*,† |
| Kidney/Tibia, mg/mm (n) | - | - | 12.8±0.8 (10) | 13.8±0.4 (9) | 30.4±5.2 *(7) | 16.6±0.7 (7)*,† |

Data (n=5-21) are mean±s.e.m.
P<0.01, *P<0.001 vs. young (4 month-old); †P<0.05 vs. wild type (WT).
BP, blood pressure.

Glomerulosclerosis injury score (GIS). Data (n=6-8) are mean±s.e.m. P<0.01, *P<0.001 vs. young (4 mo); ††P<0.01 vs. same aged wild type (Gper+/+).

Fig. 28

Blood Pressure

|  | 4-month old | | 12-month old | | 24-month old | |
| --- | --- | --- | --- | --- | --- | --- |
|  | WT | KO | WT | KO | WT | KO |
| Systolic BP, mmHg (n) | 119±2 (12) | 117±2 (8) | 121±2 (6) | 119±1 (7) | 114±2 (5) | 110±5 (5) |
| Diastolic BP, mmHg (n) | 91±2 (12) | 90±1 (8) | 89±2 (6) | 90±1 (7) | 87±2 (5) | 83±1 (5) |

Vascular Reactivity of the Renal Artery

METHOD FOR TREATING OBESITY, DIABETES, CARDIOVASCULAR AND KIDNEY DISEASES BY REGULATING GPR30/GPER ACTIVITY

RELATED APPLICATIONS

This application is a division of U.S. patent application Ser. No. 16/033,088, filed Jul. 11, 2018, now U.S. Pat. No. 10,471,047, issued Nov. 12, 2019, which is a division of U.S. patent application Ser. No. 15/556,055, filed Sep. 6, 2017, now U.S. Pat. No. 10,251,870, issued Apr. 9, 2019, which is a United States national phase patent application of International Patent Application No. PCT/US2016/020452 filed Mar. 2, 2016, which claims priority from U.S. provisional application No. U.S. 62/129,224, filed 6 Mar. 2015, entitled "Method for Treating Obesity and Diabetes by Activating GPR30/GPER, provisional application no. U.S. 62/136,820, filed Mar. 23, 2015, entitled "Targeting GPR30/GPER for Treatment of Chronic, Non-Communicable Disease Conditions Involving Excessive Formation of Reactive Oxygen Species and provisional application No. U.S. 62/217,434, filed Sep. 11, 2015, entitled, "Inhibition of NOX and NOX-Associated Reactive Oxygen Species for Treatment of Chronic, Non-communicable Disease Conditions", the entire contents of each of said applications being incorporated by reference in their entirety herein.

GOVERNMENT SUPPORT

This invention was made with government support under grant nos. CA127731 and CA163890 awarded by the National Institutes of Health. The government has certain rights in the invention.

FIELD OF THE INVENTION

The present invention is directed to the use of compounds that modulate one or more of ERalpha/beta and GPR30/GPER receptors and related pathways, to pharmaceutical compositions based upon those compounds and to methods of treating obesity and diabetes by activating the G-protein coupled estrogen receptor (GPER/GPR30) with modulators (agonists) of GPER/GPR30.

The present invention also relates to the use of compounds that modulate the expression/upregulation of nox and nox-associated reactive oxygen species (ROS) through the inhibition of one or more of GPR30/GPER and related pathways, to pharmaceutical compositions based upon those compounds and to methods of treating disease states and/or conditions including cardiovascular and other diseases, especially kidney diseases and/or conditions as otherwise disclosed herein that involve excessive formation of reactive oxygen species. The present invention is therefore directed to a method to improve the outcome of disease states and conditions in which reactive oxygen species are overproduced (upregulated) by means of inhibiting and/or reducing the production of nox and nox-associated reactive oxygen species (ROS) through inhibition of this newly identified receptor.

BACKGROUND/OVERVIEW OF THE INVENTION

Estrogens mediate multiple complex physiological responses throughout the body. The responses are in turn mediated through the binding of estrogen to receptors. The classical receptors for steroids such as estrogen are soluble cytoplasmic/nuclear proteins that function as transcription factors. These receptors are known as estrogen receptor alpha and beta (two closely related proteins) and their various splice variants that mediate transcriptional activity as well as rapid cellular signaling. GPR30/GPER is a 7-transmembrane G protein-coupled receptor that has previously been suggested by Filardo et al., to mediate estrogen-dependent signal transduction. We have demonstrated that GPR30/GPER is largely an intracellular protein, found in the endoplasmic reticulum, that binds estrogen with high affinity ($K_d$~6 nM) and mediates rapid cellular responses including calcium mobilization and phosphatidylinositol 3,4,5 trisphosphate production in the nucleus.

The current invention is in the field of molecular biology/pharmacology and provides compounds that modulate, particularly in a selective manner, the effects of GPR30/GPER and/or the classical estrogen receptors alpha and beta (ERα and ERβ). These compounds may function as agonists and/or antagonists of one or more of the disclosed estrogen receptors, particularly GPR30/GPER. Diseases which are mediated through one or more of these receptors include cancer (particularly breast, reproductive and other hormone-dependent cancers, leukemia, colon cancer, prostate cancer), reproductive (genito-urological) including endometritis, prostatitis, polycystic ovarian syndrome, bladder control, hormone-related disorders, hearing disorders, cardiovascular conditions including hot flashes and profuse sweating, hypertension, stroke, obesity, osteoporosis, hematologic diseases, vascular diseases or conditions such as venous thrombosis, atherosclerosis, among numerous others and disorders of the central and peripheral nervous system, including depression, insomnia, anxiety, neuropathy, multiple sclerosis, neurodegenerative disorders such as Parkinson's disease and Alzheimer's disease, as well as inflammatory bowel disease, Crohn's disease, coeliac (celiac) disease and related disorders of the intestine, fibrotic disease and/or conditions including pulmonary fibrosis, pulmonary hypertension, nephropathy (e.g. membranous nephropathy (MN), diabetic nephropathy and hypertensive nephropathy), glomerulonephritis (e.g. membranous glomerulonephritis and membranoproliferative glomerulonephritis (MPGN) such as rapidly progressive glomerulonephritis (RPGN)), interstitial nephritis, lupus nephritis, idiopathic nephrotic syndrome (INS) (e.g. minimal change nephrotic syndrome (MCNS) and focal segmental glomerulosclerosis (FSGS)), obstructive uropathy, polycystic kidney disease (e.g. Autosomal Dominant Polycystic Kidney Disease (ADPKD) and Autosomal Recessive Polycystic Kidney Disease (ARPKD)), liver fibrosis; cardiovascular: atherosclerosis, myocardial infarction, stroke, arterial hypertension, coronary artery disease, restenosis after balloon angioplasty, ischemia/reperfusion injury after myocardial or cerebral infarction, hypertrophic cardiomyopathy, heart failure, heart failure associated with aging (in particular diastolic dysfunction, also known as heart failure with preserved ejection fraction); renal disease states and/or conditions, including chronic kidney disease, glomerulosclerosis, proteinuric renal disease, hypertensive renal disease and nephropathy. Compounds according to the present invention may also be used as contraceptive agents to prevent or decrease the likelihood that a woman will become pregnant as a consequence of intercourse.

The invention relates to compounds that have been identified as being agonists or antagonists to one or more of these receptors and represent compounds that may be used to treat any one or more diseases or conditions mediated through these receptors. These compounds, due to their ability to bind selectively to GPR30/GPER and/or one or both of estrogen receptors (alpha and beta) are useful for the treatment or prevention of the diseases that are mediated through GPR30/GPER and/or one or both of the alpha and beta estrogen receptors.

Oxidative stress is a key determinant of cardiovascular aging, arterial hypertension, and heart failure. An essential source of reactive oxygen species (ROS) is the family of NADPH oxidase (Nox) enzymes. Nox1 is the primary inducible, superoxide-generating Nox subunit in vascular smooth muscle of large arteries with upregulated expression levels in hypertension. Sustained blood pressure increases in response to angiotensin II (Ang II), a potent vasoconstrictor peptide centrally involved in cardiovascular redox signaling, are blunted in Nox1-deficient mice. Conversely, overexpression of Nox1 exacerbates pressor responses to Ang II. Increased Nox1-derived oxidative stress has also been implicated in cardiac remodeling, myocardial fibrosis, and diastolic dysfunction. Therefore, targeting Nox1-dependent ROS production may be effective to inhibit pathological alterations in vascular tone and myocardial function.

Deletion of Gper, a 7-transmembrane G protein-coupled receptor also known to signal in response to estrogen, results in insulin resistance, glucose intolerance, obesity, and a pro-inflammatory state, increases vascular tone, whereas its activation induces vasodilation independent of sex. Furthermore, in a transgenic rat model of Ang II-dependent hypertension that is characterized by increased oxidative stress, selective GPER activation reduces vascular tone and blood pressure. Therefore, deletion of Gper would increase cardiovascular ROS production. Unexpectedly, eliminating constitutive GPER activity largely abolished Ang II-induced, Nox-mediated superoxide generation. This led us to investigate whether GPER might be involved in the regulation of Nox1 activity and in pathologies associated with increased oxidative stress in vivo, including arterial hypertension and cardiovascular aging.

BRIEF DESCRIPTION OF THE FIGURES

Suppl.

Suppl.

Suppl.

Suppl.

Suppl.

Suppl. FIG. 20, Table 1 shows echocardiographic parameters of aged Gper$^{+/-}$ and Gper$^{-/-}$ mice. Blood pressure was determined by a non-invasive tail cuff volume-pressure recording system. Data (n=3-7 per group) are means±s.e.m. IVS, interventricular septal thickness; PW, posterior wall thickness; LVEDD, left ventricular end-diastolic diameter; LVESD, left ventricular end-systolic diameter; LV, left ventricle; EF, ejection fraction; E/A ratio, mitral inflow E wave relative to A wave velocity.

FIGS. 21-30 show the results obtained from experiments that demonstrate GPER deficiency (Gper deficient mice) protects from age-related chronic kidney disease and renal vascular dysfunction.

FIG. 21 shows certain physiological characteristics of animals used in the experiments. The data (n=5-21) are means±s.e.m. P<0.01, *P<0.001 vs. young (4 month-old); †P<0.05 vs. wild type (WT). BP, blood pressure. Note the favorable impact on the kidneys the tested animals at 24 months.

FIG. 22 shows the glomerulosclerosis injury score (GIS) for test animals. Data(n=6-8) are means±s.e.m. P<0.01, *P<0.001 vs. young (4 mo); ††P<0.01 vs. same aged wild type ($Gper^{+/+}$).

FIG. 23 shows representative photomicrographs of glomeruli from aged (24 month-old) wild type ($Gper^{+/+}$) and GPER KO ($Gper^{-/-}$) mice as tested. Periodic acid Schiff (PAS) staining. Bar=50 mm.

FIG. 24 shows tubulo-interstitial injury score of test animals in the studies conducted. The tubulo-interstitial injury score (TIS) was determined in the kidneys of wild type ($Gper^{+/+}$) and GPER KO ($Gper^{-/-}$) mice. Data (n=6-8) are means±s.e.m. P<0.01, *P<0.001 vs. young (4 mo); ††P<0.01 vs. wild type ($Gper^{+/+}$).

FIG. 25 shows structural kidney injury (amyloidosis) of test animals in the studies conducted. The structural kidney injury assessed using fluorescence cytochemistry for wild type ($Gper^{+/+}$) and GPER KO ($Gper^{-/-}$) mice. Data (n=6-8) are means±s.e.m. No injury present at 4 months of age. P<0.01, *P<0.001 vs. young (4 mo); ††P<0.01 vs. same aged wild type ($Gper^{+/+}$).

FIG. 26 shows vascular injury of test animals in the studies conducted. Vascular injury score (VIS) was determined in the cortex of kidneys of wild type ($Gper^{+/+}$) and GPER KO ($Gper^{-/-}$) mice. Data (n=6-8) are means±s.e.m. **P<0.01 vs. young (4 mo); †P=0.09 vs. wild type ($Gper^{+/+}$).

FIG. 27 shows proteinuria in 24 month old test animals in the studies conducted. Proteinuria in 24 month-old WT ($Gper^{+/+}$) and GPER-deficient ($Gper^{-/-}$) mice. Data (n=4-6) are means±s.e.m. *P<0.03 vs. wild type ($Gper^{+/+}$).

FIG. 28 shows blood pressure results from test animals in the studies conducted. Presented are systolic and diastolic blood pressure in 4 month-old, 12 month-old, and 24 month-old WT ($Gper^{+/+}$) and GPER-deficient ($Gper^{-/-}$) mice. Data (n=5-12) are means±s.e.m.

FIG. 29 shows endothelium-dependent vasodilation of renal arteries in test animals. The graph shows endothelium-dependent vasodilation to acetylcholine in renal arteries from 24 month-old WT ($Gper^{+/+}$) and GPER-deficient ($Gper^{-/-}$) mice. Data (n=6-8) are means±s.e.m. *P<0.05 vs untreated; ***P<0.001 vs. young; †††P<0.001 vs. same aged wild type. gp91ds-tat, Nox1/2 inhibitor.

FIG. 30 shows vasoconstriction to angiotensin II (Ang II) in renal arteries from young and 24 month-old WT ($Gper^{+/+}$) and Gper-deficient ($Gper^{-/-}$) mice. Data (n=6-8) are means±s.e.m. *P<0.05 vs untreated; †P<0.05 vs. wild type. gp, gp91ds-tat (Nox1/2 inhibitor).

BRIEF DESCRIPTION OF THE INVENTION

Figure 1:
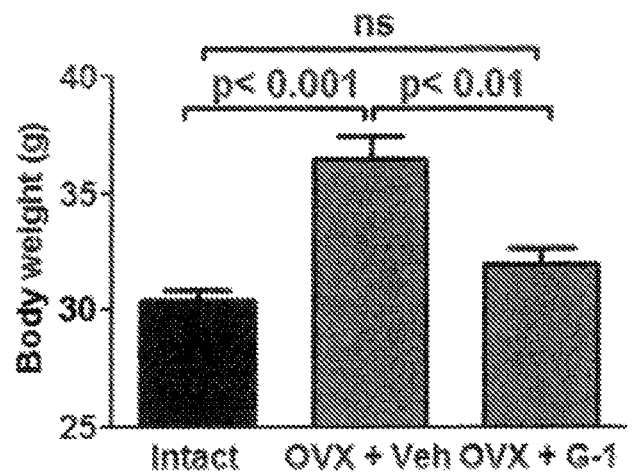
FIG. 1 shows treatment with GPER selective agonist, G-1 in ovariectomized (OVX) females (A) and high fat diet (HFD) male mice (B) attenuates weight gain over the respective controls (Veh). Intact=ovary intact control females, NC=normal chow control diet.
Figure 1:
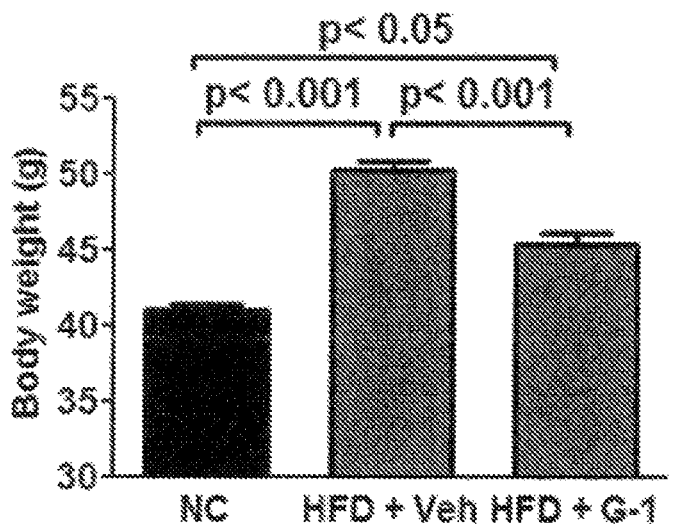
Figure 2:
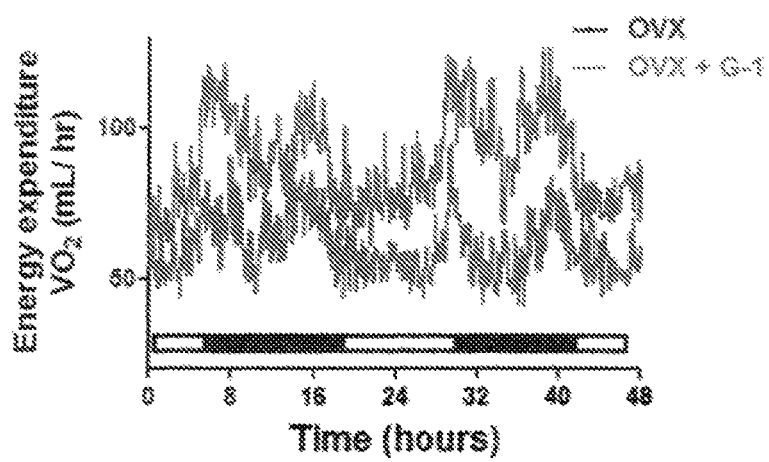
FIG. 2 shows increased energy expenditure with G-1 treatment in ovariectomized (OVX) females (A) and high fat diet (HFD) male mice (B).
Figure 2:
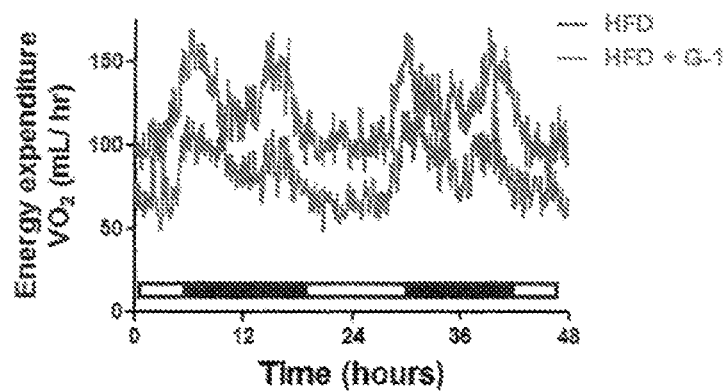
Figure 3:
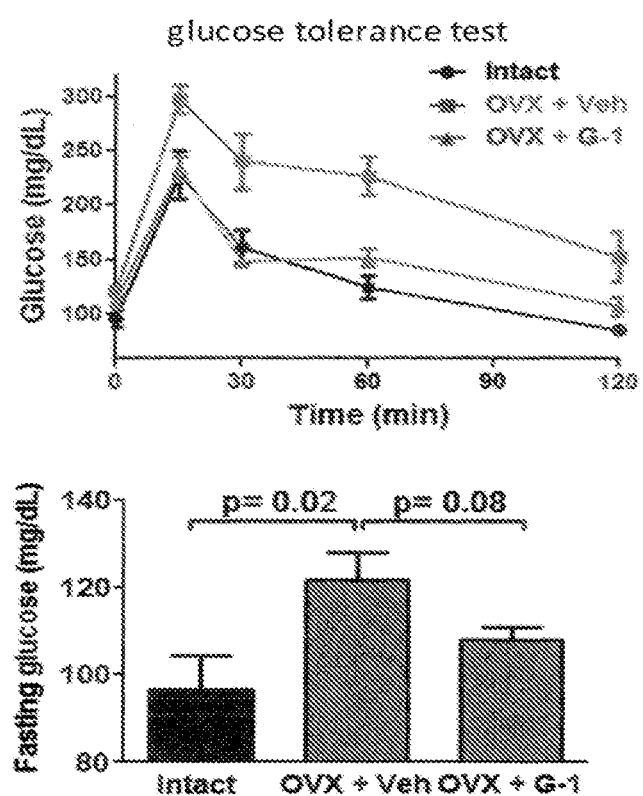
FIG. 3 shows G-1 treatment in ovariectomized (OVX) females (A) and high fat diet (HFD) male mice (B) improves glucose tolerance (by glucose tolerance test), decreases fasting blood glucose and enhances insulin sensitivity (by insulin tolerance test).
Figure 3:
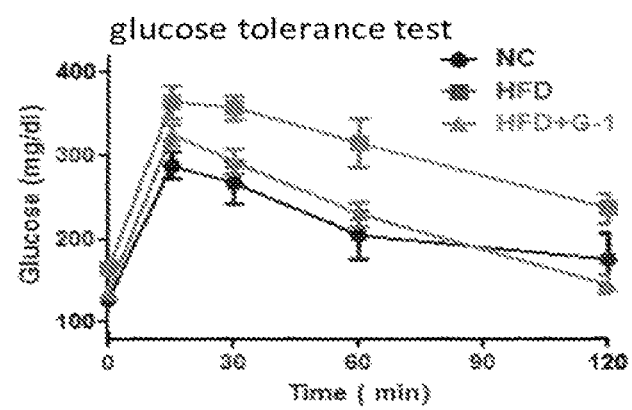
Figure 3:
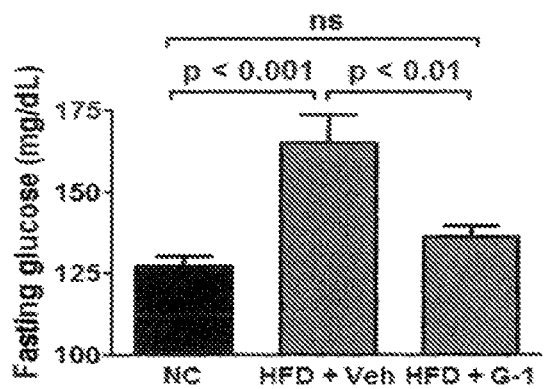
Figure 3:
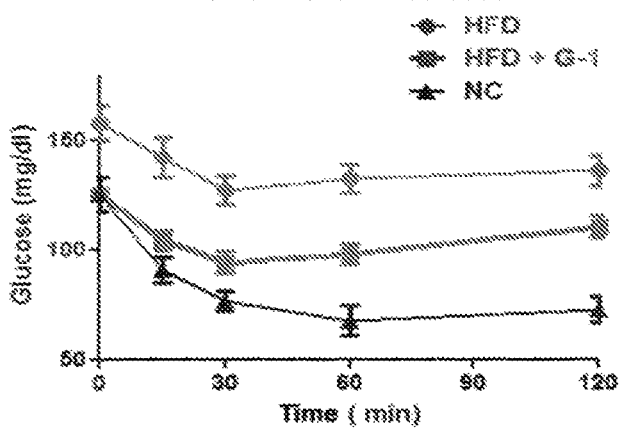
Figure 4:
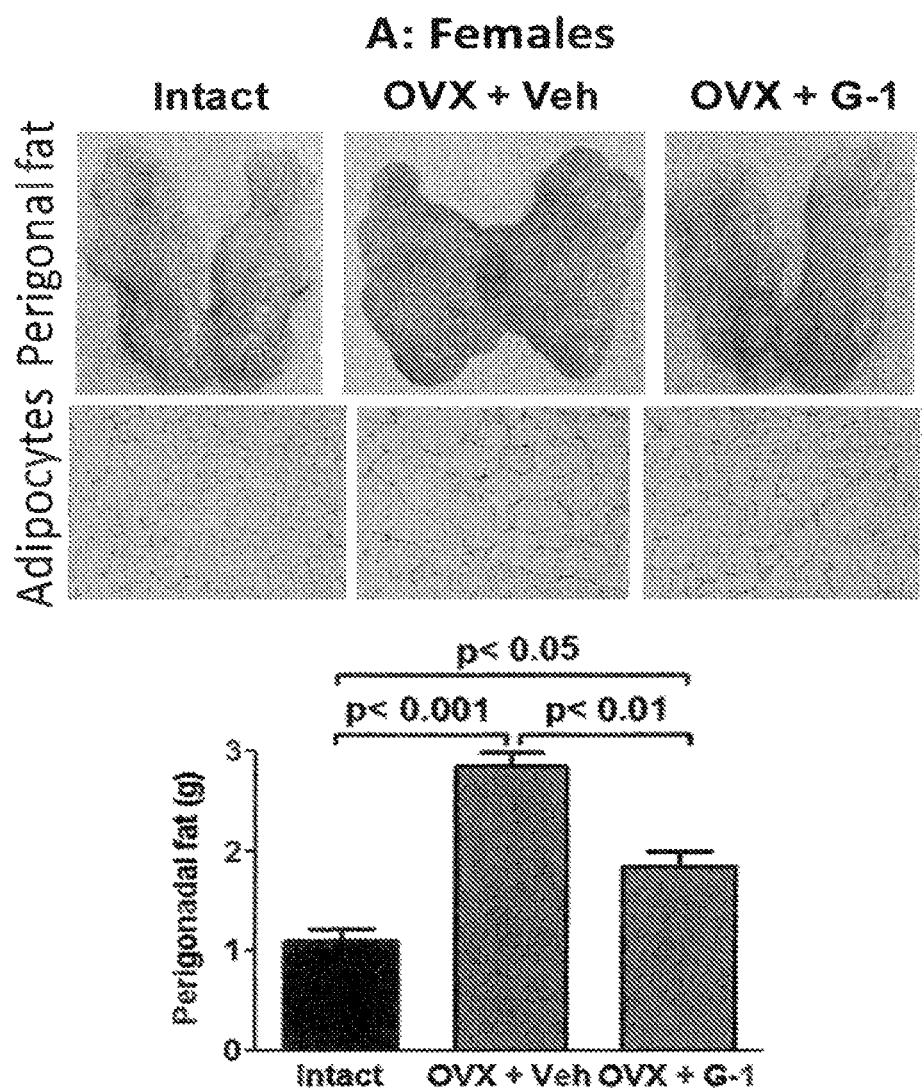
FIG. 4 shows treatment with G-1 in ovariectomized females (OVX) (A) and high fat diet (HFD) males (B) decreases visceral adiposity as exhibited by lower perigonadal, perirenal or liver weights and smaller adipocytes in perigonadal fat.
Figure 4:
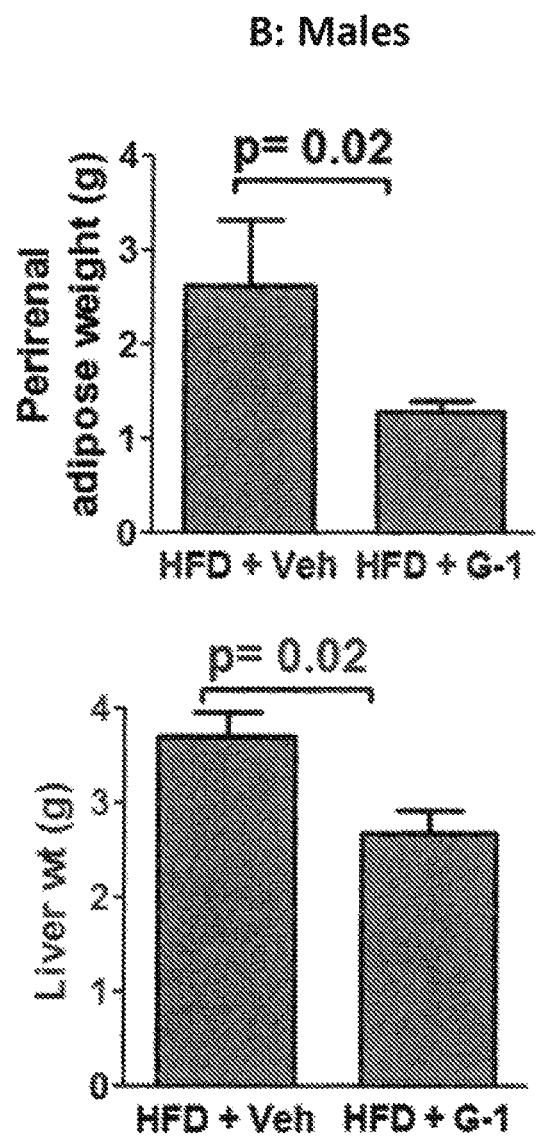

In one embodiment, the present invention is directed to compounds that are GPR30/GPER-targeted inhibitors of the expression of Nox (NADPH oxidase) isoforms (nox and nox-associated reactive oxygen species) so that these isoforms are decreased, resulting in favorable therapy of numerous disease states and conditions which are modulated through these isoforms. The present invention is also directed to a method of treating a disease state or condition which occurs as a consequence of the upregulation of nox and nox-associated reactive oxygen species comprising administering a compound that modulates (inhibits) the expression of these reactive oxygen species, to provide a favorable therapeutic outcome to such a disease state and/or condition. The present invention is thus directed to compounds and methods that are useful to treat a large number of disease states and conditions, in particular cardiovascular and renal disease states and/or conditions, among others, as otherwise described herein.

The present invention relates to compounds and their use in the treatment of a disease state and/or condition which involves excessive formation of reactive oxygen species which are modulators (preferably antagonists or inhibitors) of the expression of Nox (NADPH oxidase) isoforms (nox and nox-associated reactive oxygen species) so that these isoforms are decreased and through that inhibition, treat conditions and/or disease states in which excessive formation of reactive oxygen species occurs. These disease states and/or conditions including neurodegenerative and neurological disease states and conditions, including schizophrenia, Alzheimer's, ALS, Parkinson's; fibrotic disease and/or conditions including pulmonary fibrosis, pulmonary hypertension, hypertensive nephropathy, diabetic nephropathy, liver fibrosis; cardiovascular: atherosclerosis, myocardial infarction, stroke, arterial hypertension, coronary artery disease, restenosis after balloon angioplasty, ischemia/reperfusion injury after myocardial or cerebral infarction, hypertrophic cardiomyopathy, heart failure, heart failure associated with aging (in particular diastolic dysfunction, also known as heart failure with preserved ejection fraction); renal disease states and/or conditions, including chronic kidney disease, glomerulosclerosis, proteinuric renal disease, hypertensive renal disease, nephropathy; sensory impairment, including ocular disease, hearing loss; chronic inflammation and autoimmune diseases and/or conditions including diabetes, rheumatoid arthritis and lupus; cancer, especially including renal, lung, prostate and breast cancers among numerous others; infectious diseases, including hepatitis, influenza, HIV, septic shock, among others. In one embodiment, the patient in need thereof is suffering from a disease selected from the group consisting of nephropathy (e.g. membranous nephropathy (MN), diabetic nephropathy and hypertensive nephropathy), glomerulonephritis (e.g. membranous glomerulonephritis and membranoproliferative glomerulonephritis (MPGN) such as rapidly progressive glomerulonephritis (RPGN)), interstitial nephritis, lupus nephritis, idiopathic nephrotic syndrome (INS) (e.g. minimal change nephrotic syndrome (MCNS) and focal segmental glomerulosclerosis (FSGS)), obstructive uropathy, polycystic kidney disease (e.g. Autosomal Dominant Polycystic Kidney Disease (ADPKD) and Autosomal Recessive Polycystic Kidney Disease (ARPKD)), cardiovascular diseases, hypertension, diabetes, and kidney graft rejection (e.g. acute and chronic kidney rejection). In one embodiment, the present invention is directed to the treatment of renal disease states and/or conditions, including renal injury as described herein.

The present invention also is directed to methods of treating obesity and/or diabetes (I or II) and related disease states and/or conditions such as prediabetes, insulin resistance, retinopathy, neuropathy, nephropathy and cardiovascular diseases (coronary artery disease, angina, myocardial infarction, stroke and atherosclerosis).

Thus, the present invention relates to a method of treating of treating disease states and conditions which involve excessive formation of reactive oxygen species or alternatively, obesity and/or diabetes using at least one compound according to the chemical structure I:

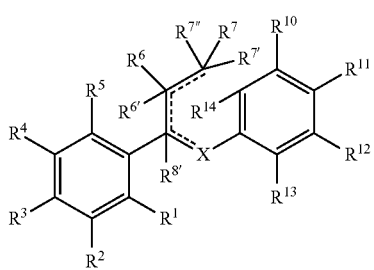

Where X is =N—, O, S, or N—R, with the proviso that when X is N—R and R is a bond, N together with $R^1$ forms a 5- to 7-membered optionally substituted heterocyclic group;

R is a bond, H, OH, $NO_2$, an optionally substituted $C_1$-$C_6$ hydrocarbyl, preferably an optionally substituted alkyl, an optionally substituted aryl, an optionally substituted heteroaryl, an optionally substituted heterocycle, an optionally substituted —C(O)—($C_1$-$C_6$) alkyl (amide), an optionally substituted —C(O)—O—($C_1$-$C_6$) alkyl (urethane), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheterocycle);

$R^1$, $R^2$ and $R^5$ are each independently selected from H, OH, $NO_2$, halogen (F, Br, Cl or I), a $C_1$-$C_6$ optionally substituted carboxylic acid group, an optionally substituted O—($C_1$-$C_6$)alkyl, optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheterocycle);

$R^3$ and $R^4$ are each independently selected from H, OH, $NO_2$, halogen (F, Br, Cl or I), a $C_1$-$C_6$ optionally substituted carboxylic acid group, an optionally substituted O—($C_1$-$C_6$) alkyl, an optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheteroaryl) or $R^3$ and $R^4$ together form a 5- or 6-membered optionally substituted carbocyclic (which may be saturated or unsaturated), optionally substituted aryl, optionally substituted heteroaryl or optionally substituted heterocyclic group;

$R^6$ and $R^7$ are each independently absent or are selected from H, OH, $NO_2$, halogen (F, Br, Cl or I), a $C_1$-$C_6$ optionally substituted carboxylic acid group, an optionally substituted O—($C_1$-$C_6$)alkyl, an optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheteroaryl), or together $R^6$ and $R^7$ form a 4-, 5-, 6- or 7-membered optionally substituted carbocyclic (which may be saturated or unsaturated), an optionally substituted aryl, optionally substituted heteroaryl or optionally substituted heterocyclic group, or a 5- to 9-membered optionally substituted carbocyclic or heterocyclic bicyclic group, with the proviso that $R^7$ is not absent when both $R^{7'}$ and $R^{7''}$ are also absent;

$R^{6'}$ is absent, H, a $C_1$-$C_6$ optionally substituted hydrocarbyl group (preferably H, $CH_3$ or $CH_2CH_3$) or together with $R^6$ forms a =O group;

$R^{7'}$ is absent, H, optionally substituted hydrocarbyl group (preferably H, $CH_3$ or $CH_2CH_3$), or together with $R^7$ forms a =O group;

$R^{7''}$ is absent, H, OH, halogen (F, Br, Cl or I), an optionally substituted O—($C_1$-$C_6$)alkyl, an optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheteroaryl);

$R^{8'}$ is absent (when the carbon to which $R^{8'}$ is attached and the carbon to which $R^6$ is attached form an optional double bond), H, $CH_3$ or $CH_2CH_3$;

$R^{10}$, $R^{11}$, $R^{12}$ and $R^{13}$ are each independently H, OH, $NO_2$, halogen (F, Br, Cl or I), a $C_1$-$C_6$ optionally substituted carboxylic acid group, an optionally substituted O—($C_1$-$C_6$) alkyl, an optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheterocyclyl);

$R^{14}$ is H, OH, $NO_2$, halogen (F, Br, Cl or I), a $C_1$-$C_6$ optionally substituted carboxylic acid group, an optionally substituted O—($C_1$-$C_6$)alkyl, optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheterocyclyl) or together with the carbon to which $R^7$ is attached forms a 5-, 6- or 7-membered optionally substituted carbocyclic (which may be saturated or unsaturated), optionally substituted aryl, optionally substituted heteroaryl or optionally substituted heterocyclic ring; or a stereoisomer, pharmaceutically acceptable salt, solvate, or polymorph thereof. These compounds are disclosed in U.S. Pat. No. 7,875,721, the entire contents of which is incorporated by reference herein.

Preferred compounds according to the present invention relate to compounds according to the chemical structure II:

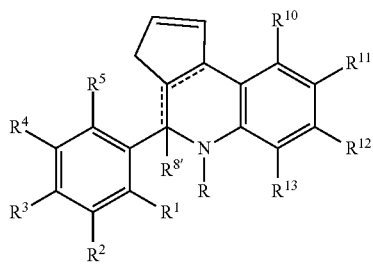

II

Where R, $R^1$, $R^2$, $R^3$, $R^4$, $R^5$, $R^{8'}$, $R^{10}$, $R^{11}$, $R^{12}$ and $R^{13}$ are as previously described above, or a stereoisomer, pharmaceutically acceptable salt, solvate, or polymorph thereof.

Preferred compounds according to the present invention also relate to compounds according to the chemical structure III:

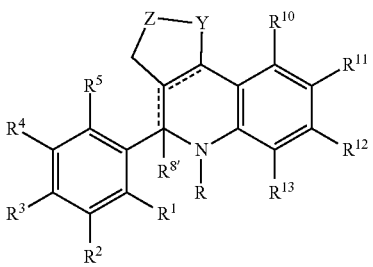

III

Where R, $R^1$, $R^2$, $R^3$, $R^4$, $R^5$, $R^{8'}$, $R^{10}$, $R^{11}$, $R^{12}$ and $R^{13}$ are as previously described above;

Y is an optionally substituted $(CH_2)_n$ group where n is 0, 1 or 2, an optionally substituted =CH— group, a C=O group, O, S, optionally substituted N—($C_1$-$C_6$)alkyl, optionally substituted N-aryl, optionally substituted N-heteroaryl, optionally substituted N-heterocycle, optionally substituted N—C(O)—($C_1$-$C_6$)alkyl, optionally substituted N—C(O)-aryl, optionally substituted N—C(O)-heteroaryl, optionally substituted N—C(O)-heterocycle; or a stereoisomer, pharmaceutically acceptable salt, solvate, or polymorph thereof;

Z is an optionally substituted $(CH_2)_n$ group where n is 1 or 2, an optionally substituted =CH— group, a C=O group, O, S, optionally substituted N—($C_1$-$C_6$)alkyl, optionally substituted N-aryl, optionally substituted N-heteroaryl, optionally substituted N-heterocycle, optionally substituted N—C(O)—($C_1$-$C_6$)alkyl, optionally substituted N—C(O)-aryl, optionally substituted N—C(O)-heteroaryl, optionally substituted N—C(O)-heterocycle; or a stereoisomer, pharmaceutically acceptable salt, solvate or polymorph thereof.

In preferred aspects of the invention, $R^3$ and $R^4$ form a five membered heterocyclic ring, preferably having two heteroatoms. Preferably, $R^3$ and $R^4$ form a furan ring. In preferred aspects of the invention, R is H or a $C_1$-$C_3$ alkyl group. In preferred embodiments according to the present invention, at least one of $R^1$, $R^2$, $R^5$, $R^{10}$, $R^{11}$, $R^{12}$ and $R^{13}$ and as many as three of these substituents is a halogen group. In certain preferred embodiments one of these $R^1$, $R^2$, $R^5$, $R^{10}$, $R^{11}$, $R^{12}$ and $R^{13}$ groups is a $(CH_2)_n$—$NH_2$ group, where n is 1-6, preferably 1, 2 or 3, preferably 2, where the amino group can be further reacted to provide a fluorescent label. In certain preferred embodiments, $R^1$, $R^2$ or $R^5$ is a halogen (preferably F or Br) or an optionally substituted $C_1$-$C_6$ hydrocarbyl group (alkyl or a $C_2$-$C_6$ alkenyl or alkynyl) or a —O—($C_1$-$C_6$ alkyl) group and $R^{11}$ or $R^{12}$ is a halogen, a $C_2$-$C_6$ acyl group (preferably, acetyl), a carboxyl acid group, an optionally substituted (with at least one $C_1$-$C_3$ alkyl group) carboxamido group, a —O—($C_1$-$C_6$ alkyl) group or an optionally substituted ester group (—C(O)O—($C_1$-$C_6$ alkyl) or —O—C(O)—($C_1$-$C_6$ alkyl)).

Preferred compounds for use in the present invention are compounds according to the following structure.

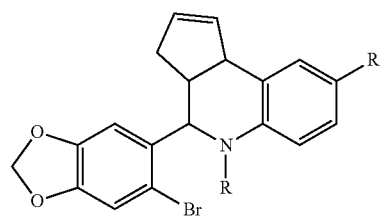

Where R is H, an acetyl group or an isopropyl group, or an isomer, diastereomer, enantiomer, or pharmaceutically acceptable salt, solvate or polymorph thereof.

In alternative embodiments, the modulator compounds are as follows:

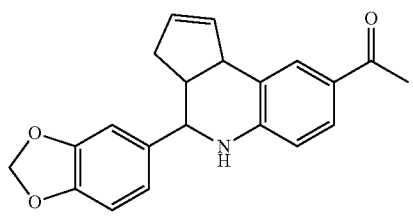

13
-continued
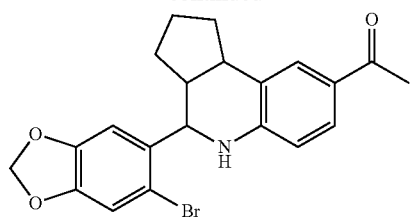
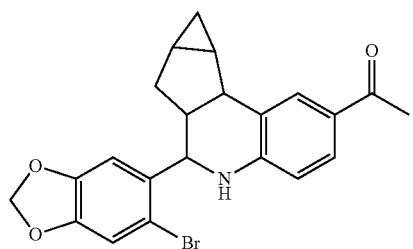
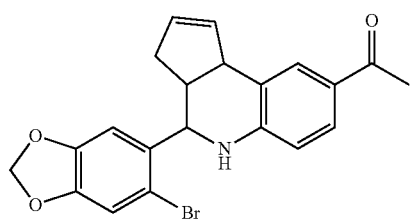
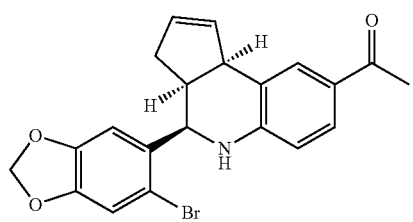
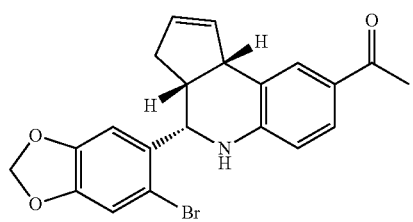
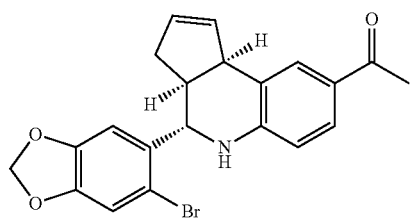
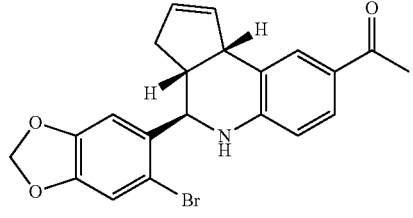
14
-continued
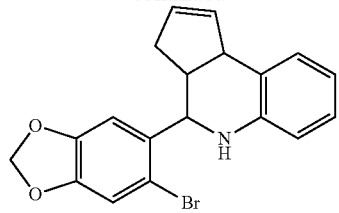
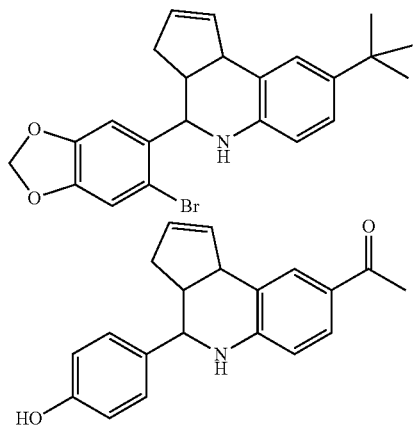
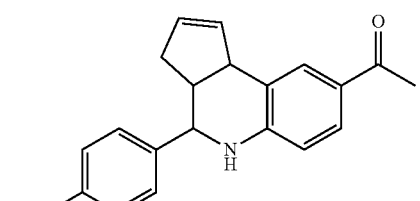
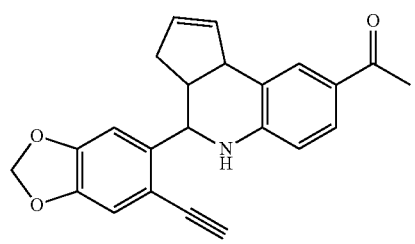
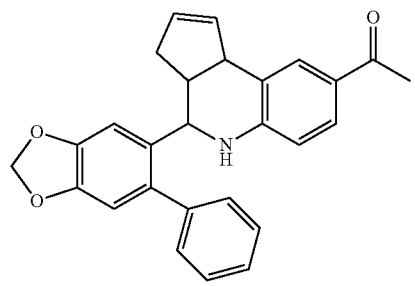
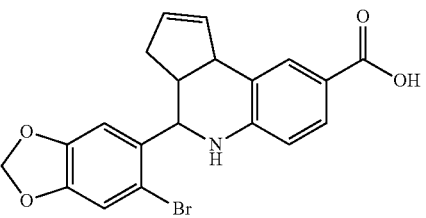

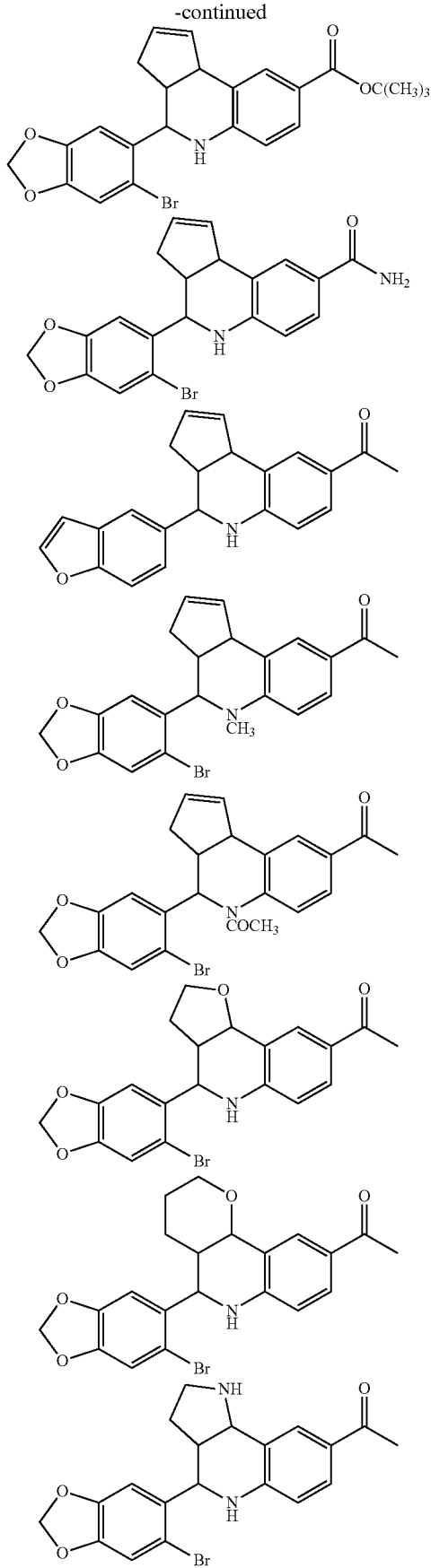

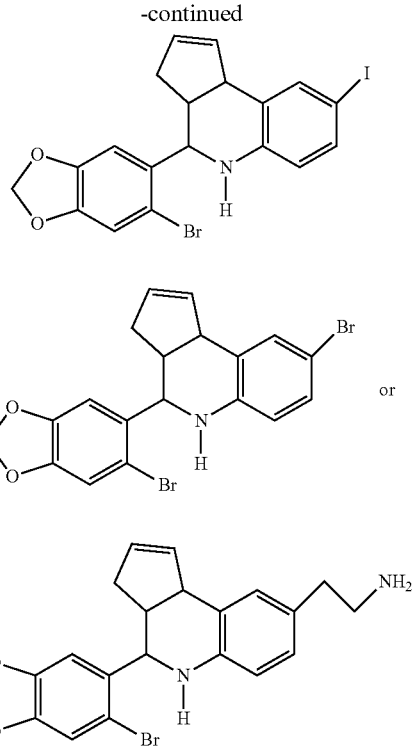

Or a pharmaceutically acceptable salt or enantiomer thereof.

In certain embodiments, the preferred compounds are

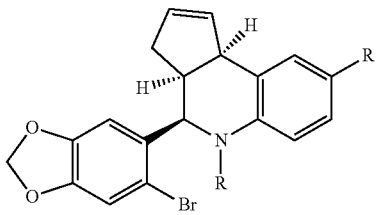

Where R is H (compound G15) or an isopropyl group (compound G36), or a pharmaceutically acceptable salt thereof.

In other embodiments, a particularly preferred compound (G1) for use in the present invention is a compound according to the following structure.

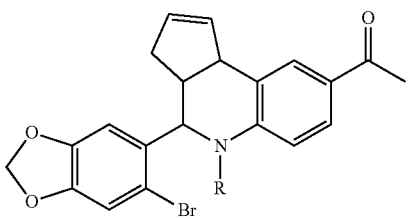

or an isomer, diastereomer, enantiomer, or pharmaceutically acceptable salt, solvate or polymorph thereof.

An even more preferred compound is

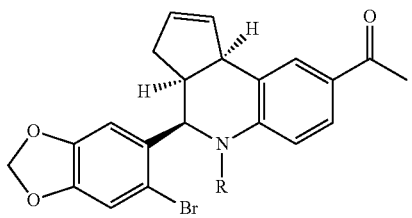

or
a pharmaceutically acceptable salt thereof.

The above compounds are known in the art as GPR30/GPER modulators (agonists and/or inhibitors). It has unexpectedly been discovered that the modulation, especially the inhibition of GPR30/GPER, has an impact (modulation) on superoxide production and Nox expression (particularly Nox1) and inhibits and/or reduces the likelihood of an overproduction (upregulation) of reactive oxygen species (ROS), which is involved in many disease states and conditions as otherwise described herein. These compounds, particularly agonists, are also active to reduce obesity/diabetes and related disease states and conditions such as weight gain, inflammation, prediabetes and insulin resistance, among others, through the regulation of cellular signaling pathways, particularly PI3kinase, Akt and AMPK. These modulators, especially inhibitors of GPR30/GPER, also represent a previously unknown therapeutic option for the treatment of many disease states which involve and/or are negatively impacted by an upregulation of reactive oxygen species (ROS).

In one embodiment, the present invention also relates to pharmaceutical compositions comprising an effective amount of one or more of the above-referenced compounds, optionally in combination with a pharmaceutically acceptable additive, carrier or excipient and further optionally in combination with at least one additional anti-obesity and/or anti-diabetes drug.

In another embodiment, the present invention also relates to pharmaceutical compositions comprising an effective amount of one or more of the above-referenced compounds, optionally in combination with a pharmaceutically acceptable additive, carrier or excipient and further optionally in combination with at least one additional bioactive agent, preferably a drug which also treats one or more of the disease states and/or conditions treated by the present invention.

In one embodiment, the present invention relates to compounds and their use in the treatment of obesity and/or diabetes which preferably are modulators (preferably agonists) of GPR30/GPER and/or alpha and/or beta estrogen receptor and act through their action at one or more of these receptors, can be used to treat or reduce the likelihood or diseases or conditions which are modulated through those receptors, especially obesity, insulin resistance, glucose dysregulation and diabetes.

The compounds according to the present invention can be used to modulate GPR30/GPER and/or alpha and/or beta estrogen receptors in the treatment of obesity and/or diabetes (especially type II diabetes). Compounds according to the present invention have antagonist and/or agonist activity, preferably agonist activity against these receptors. Compounds according to the present invention can be used to treat obesity and/or diabetes, which unexpectedly has been discovered to be mediated through these receptors.

The present invention relates to compounds and their use in the treatment of a disease state and/or condition, which involves excessive formation of reactive oxygen species, acting as modulators (preferably antagonists) or inhibitors of the expression and activity of Nox (NADPH oxidase) isoforms (nox and nox-associated reactive oxygen species) so that these isoforms are decreased and treat conditions and/or disease states in which excessive formation of reactive oxygen species occurs. These disease states and/or conditions include neurodegenerative and neurological disease states and conditions, including schizophrenia, Alzheimer's, ALS, Parkinson's; fibrotic disease and/or conditions including pulmonary fibrosis, pulmonary hypertension, hypertensive nephropathy, diabetic nephropathy, liver fibrosis; cardiovascular: atherosclerosis, myocardial infarction, stroke, arterial hypertension, coronary artery disease, restenosis after balloon angioplasty, ischemia/reperfusion injury after myocardial or cerebral infarction, hypertrophic cardiomyopathy, heart failure, heart failure associated with aging (in particular diastolic dysfunction, also known as heart failure with preserved ejection fraction); renal disease states and/or conditions as otherwise described herein, including chronic kidney disease, glomerulosclerosis, proteinuric renal disease, hypertensive renal disease, nephropathy; sensory impairment, including ocular disease, hearing loss; chronic inflammation and autoimmune diseases and/or conditions including diabetes, rheumatoid arthritis and lupus; cancer, especially including renal, lung, prostate and breast cancers among numerous others; infectious diseases, including hepatitis, influenza, HIV, septic shock, among others. In one embodiment, the patient in need thereof is suffering from a renal disease or condition selected from the group consisting of nephropathy (e.g. membranous nephropathy (MN), diabetic nephropathy and hypertensive nephropathy), glomerulonephritis (e.g. membranous glomerulonephritis and membranoproliferative glomerulonephritis (MPGN) such as rapidly progressive glomerulonephritis (RPGN)), interstitial nephritis, lupus nephritis, idiopathic nephrotic syndrome (INS) (e.g. minimal change nephrotic syndrome (MCNS) and focal segmental glomerulosclerosis (FSGS)), obstructive uropathy, polycystic kidney disease (e.g. Autosomal Dominant Polycystic Kidney Disease (ADPKD) and Autosomal Recessive Polycystic Kidney Disease (ARPKD)), cardiovascular diseases, hypertension, diabetes, and kidney graft rejection (e.g. acute and chronic kidney rejection).

Pursuant to the present invention, it has been found that elimination of GPER expression inhibited and/or reduced the likelihood of the development of age-related hypertrophy, fibrosis and the associated functional impairment (diastolic dysfunction, clinically evident as heart failure with preserved ejection fraction) as wall as the development of arterial hypertension induced by chronic angiotensin infusion. In addition, treatment of mice with a GPER-selective antagonist, such as G36 (specific isomer above, R is isopropyl), reduced hypertension and normalized arterial function. Based on these observations, we posit that GPER antagonists, including compounds G15 and G36 (see above), have a therapeutic potential in treating the disease states listed above that involve the excessive formation of oxygen-derived free radicals (ROS).

The compounds according to the present invention can be used to modulate/inhibit the formation of reactive oxygen species (reduce oxidative stress) in the treatment of disease states and conditions in which reactive oxygen species are involved. Compounds according to the present invention have antagonist and/or agonist activity, preferably agonist activity against these receptors. Compounds according to the present invention can be used to treat disease states and/or conditions in which reactive oxygen species are elevated (excessive formation) as described herein.

A method of treating any one or more of the above-described diseases or conditions comprises administering to a patient in need thereof at least one compound as otherwise described herein or a pharmaceutically acceptable salt thereof, optionally in combination with a pharmaceutically acceptable carrier, additive or excipient, optionally in combination with at least one additional bioactive agent, preferably an anti-obesity and/or anti-diabetes agent or an agent which can be used for treating any one or more of the other disease states and/or conditions which are disclosed herein principally by reducing/inhibiting the excessive formation of nox and nox-associated reactive oxygen species.

DETAILED DESCRIPTION OF THE INVENTION

The following terms shall be used throughout the specification to describe the present invention. A term, which is otherwise not defined, has the same meaning as one of ordinary skill within the context of the use of that term would assign to the term. Note that all terms are used in context to avoid overlap and redundancy where applicable.

The term "patient" refers to a mammal, preferably a human, in need of treatment or therapy to which compounds according to the present invention are administered in order to treat a condition or disease state modulated through the binding of a compound according to the present invention with a receptor, and in particular, GPR30/GPER and/or estrogen receptor alpha (ERα) and/or (ERβ).

The term "GPR30/GPER receptor" refers to a 7-transmembrane G protein-coupled receptor that mediate estrogen-dependent signal transduction. GPR30/GPER is an intracellular protein, found in the endoplasmic reticulum, which binds estrogen with high affinity ($K_d$~6 nM) and mediates rapid cellular responses including calcium mobilization and phosphatidylinositol 3,4,5 trisphosphate production in the nucleus. GPR30/GPER receptor refers to all types of GPR30/GPER receptors, regardless of the tissue in which such receptor is found and refers to any variant thereof, including receptors of mammals (preferably, humans and domesticated mammals where veterinary applications are relevant) and variants thereof. Other names that have been used for GPR30/GPER include GPER. CMKRL2, DRY12, FEG-1, GPCR-Br, LERGU, LERGU2, LyGPR, CEPR and MGC99678, among others.

The term "modulate" means, with respect to disease states or conditions modulated through GPR30/GPER and/or estrogen receptor alpha (ERα) and/or estrogen receptor beta (ERβ) and/or the expression/upregulation of nox and nox-associated reactive oxygen species, especially the upregulation of reactive oxygen species, the inhibition of these reactive oxygen species and/or the binding of a compound according to the present invention to GPR30/GPER and/or estrogen receptor alpha (ERα) and/or estrogen receptor beta (ERβ) to produce, either directly or indirectly, an improvement or lessening of a condition or disease state which was, prior to administration of a compound according to the present invention, sub-optimal and in many cases, debilitating and even life threatening. Modulation may occur by virtue of agonist activity, antagonist activity or mixed agonist/antagonist activity (depending on the receptor site) or indirectly on a pathway related to same.

The term "compound", as used herein, unless otherwise indicated, refers to any specific chemical compound disclosed herein regardless of disease state and/or condition treated or by what mechanism such effect occurs and includes in context, tautomers, regioisomers (especially cis/trans), geometric isomers, and where applicable, optical isomers thereof, as well as pharmaceutically acceptable salts, solvates and polymorphs thereof. Within its use in context, the term compound generally refers to a single compound, but also may include other compounds such as stereoisomers, regioisomers and/or optical isomers (including in some instances, racemic mixtures) as well as specific enantiomers or enantiomerically enriched mixtures of disclosed compounds. The compounds of this invention include all stereoisomers where relevant (e.g., cis and trans isomers) and all optical isomers of the present compounds (eg., R and S enantiomers), as well as racemic, diastereomeric and/or other mixtures of such isomers, as well as all pharmaceutically acceptable salt forms, solvates, polymorphs and prodrug forms of the present compounds, where applicable.

The term "independently" is used herein to indicate that the variable, which is independently applied, varies independently from application to application.

The term "non-existent" or "absent" refers to the fact that a substituent is absent and the group to which such substituent is attached forms an additional bond with an adjacent atom or group.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

The term "obesity" and "diabetes" are used to describe conditions and/or disease states treated using compounds according to the present invention. The diabetes may also include, within context, prediabetes and/or insulin resistance because they are intimately related to same.

The term "disease state and/or condition involving excessive formation of reactive oxygen species" is used to describe conditions and/or disease states in which oxidative stress is a component of these disease states and conditions because of the upregulation in production of reactive oxygen species. These disease states and/or conditions are treated using compounds according to the present invention that are modulators of GPR30/GPER, preferably inhibitors. These disease states and/or conditions include, for example, neurodegenerative and neurological disease states and conditions, including schizophrenia, Alzheimer's, ALS, Parkinson's; fibrotic disease and/or conditions including pulmonary fibrosis, pulmonary hypertension, hypertensive nephropathy, diabetic nephropathy, liver fibrosis; cardiovascular: atherosclerosis, myocardial infarction, stroke, arterial hypertension, coronary artery disease, restenosis after balloon angioplasty, ischemia/reperfusion injury after myocardial or cerebral infarction, hypertrophic cardiomyopathy, heart failure, heart failure associated with aging (in particular diastolic dysfunction, also known as heart failure with preserved ejection fraction); renal disease states and/or conditions, including chronic kidney disease, glomerulosclerosis, proteinuric renal disease, hypertensive renal disease, nephropathy; sensory impairment, including ocular disease, hearing loss; chronic inflammation and autoimmune diseases and/or conditions including diabetes, rheumatoid arthritis and lupus; cancer, especially including renal, lung, prostate and breast cancers among numerous others; infectious diseases, including hepatitis, influenza, HIV, septic shock, among others.

The term "kidney disease or condition" means any disease state or condition in which the kidney is impaired including, for example, nephropathy (e.g. membranous nephropathy (MN), diabetic nephropathy and hypertensive nephropathy), glomerulonephritis (e.g. membranous glomerulonephritis and membranoproliferative glomerulonephritis (MPGN) such as rapidly progressive glomerulonephritis (RPGN)), interstitial nephritis, lupus nephritis, idiopathic nephrotic syndrome (INS) (e.g. minimal change nephrotic syndrome (MCNS) and focal segmental glomerulosclerosis (FSGS)), obstructive uropathy, polycystic kidney disease (e.g. Autosomal Dominant Polycystic Kidney Disease (ADPKD) and Autosomal Recessive Polycystic Kidney Disease (ARPKD)), hypertension, diabetes, and kidney graft rejection (e.g. acute and chronic kidney rejection). Kidney disease states and conditions that are treated pursuant to the present invention include renal injury, chemical or physical insult resulting in apoptosis or necrosis of renal tissue, disease, or those otherwise at risk of chronic renal failure. For example, subjects in, or at risk of, chronic renal failure, or at risk of the need for renal replacement therapy, including but not limited to the following: chronic renal failure, end-stage renal disease, chronic diabetic nephropathy, hypertensive nephrosclerosis, chronic glomerulonephritis, hereditary nephritis, and/or renal dysplasia; glomerular hypertrophy, tubular hypertrophy, chronic glomerulosclerosis, renal cell carcinoma, and/or chronic tubulointerstitial sclerosis and renal fibrosis.

Other renal disease states and conditions include renal injury, chronic renal failure, renal replacement therapy (i.e., chronic hemodialysis, continuous peritoneal dialysis, or kidney transplantation), progressive loss of renal function, including progressive loss of renal function associated with progressive loss of functioning nephron units, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, renal cell carcinoma, and/or chronic tubulointerstitial sclerosis, renal fibrosis; an unusual number of broad casts present in urinary sediment; a GFR which is chronically less than about 50%, and more particularly less than about 40%, 30% or 20%, of the expected GFR for a patient subject; GFR (in human male subjects weighing at least 50 kg) which is chronically less than about 50 ml/min, and more particularly less than about 40 ml/min, 30 ml/min or 20 ml/min; GFR (in human female subjects weighing at least about 40 kg) and having a GFR which is chronically less than about 40 ml/min, and more particularly less than about 30 ml/min, 20 ml/min or 10 ml/min; subjects possessing a number of functional nephron units which is less than about 50%, and more particularly less than about 40%, 30% or 20%, of the number of functional nephron units possessed by a healthy but otherwise similar subject; subjects which have a single kidney; and subjects which are kidney transplant recipients. Additional kidney disease states and conditions include diabetic nephropathy, renal failure, glomerulonephritis, nephrotoxicity of aminoglycosides and platinum compounds and kidney disease caused by a hyperactive bladder.

The two most common causes of chronic kidney disease are diabetes and hypertension. Other factors include acute insults from nephrotoxins, including radiocontrast agents, or decreased perfusion (ischemia); sepsis; Proteinuria; Increased renal ammoniagenesis with interstitial injury; Hyperlipidemia; Hyperphosphatemia with calcium phosphate deposition; Decreased levels of nitrous oxide; and smoking.

The term "coadministration" or "combination therapy" is used to describe a therapy in which at least two active compounds in effective amounts are used to treat a disease state or condition as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more anti-obesity and/or anti-diabetes agent or a bioactive which may be traditionally used to treat one or more other disease states and/or conditions hereof. Coadministration of one of the present compounds with another bioactive agent as otherwise described herein will often result in a synergistic enhancement of the activity of the other agent, an unexpected result. One or more of the present compounds may also be coadministered with another bioactive agent (e.g., antiviral agent, antihyperproliferative disease agent, agents which treat chronic inflammatory disease, among others or as otherwise described herein), depending upon the desired therapeutic outcome and the disease state or condition treated.

"Hydrocarbon" or "hydrocarbyl" refers to any radical containing carbon and hydrogen, which may be straight, branch-chained or cyclic in nature. Hydrocarbons include linear, branched and cyclic hydrocarbons, including alkyl groups, alkylene groups and unsaturated hydrocarbon groups, which may be optionally substituted. Hydrocarbyl groups may be fully saturated or unsaturated, containing one or more double ("ene") or triple ("yne") bonds.

"Alkyl" refers to a fully saturated monovalent hydrocarbyl radical containing carbon and hydrogen, and which may be cyclic, branched or a straight chain. Examples of alkyl groups are methyl, ethyl, n-butyl, n-hexyl, n-heptyl, n-octyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups.

"Alkylene" refers to a fully saturated hydrocarbon which is divalent (may be linear, branched or cyclic) and which is optionally substituted. Other terms used to indicate substituent groups in compounds according to the present invention are as conventionally used in the art. Thus, the term alkylene aryl includes alkylene phenyl such as a benzyl group or ethylene phenyl group, alkylaryl, includes alkylphenyl such a phenyl group which has alkyl groups as substituents, etc. The bond ══════ , when used in chemical structures of the present application refers to a single chemical bond, which may be an optional double bond, in context.

"Aryl" refers to a substituted or unsubstituted monovalent aromatic radical having a single ring (e.g., benzene) or multiple condensed rings (e.g., naphthyl, anthracenyl, phenanthryl) and can be can be bound to compound according to the present invention at any position on the ring(s). Other examples of aryl groups include heterocyclic aromatic ring sys-terms "heteroaryl" having one or more nitrogen, oxygen, or sulfur atoms in the ring, such as imidazole, furyl, pyrrole, pyridyl, indole and fused ring systems, among others, which may be substituted or unsubstituted.

"Alkoxy" as used herein refers to an alkyl group bound through an ether linkage; that is, an "alkoxy" group may be represented as —O-alkyl where alkyl is as defined above.

The term "cyclic" shall refer to a carbocyclic or heterocyclic group, preferably a 5- or 6-membered ring, but may include 4 and 7-membered rings. "Bicyclic" or "bicyclo" refers to bicyclic The term "heterocycle" or "heterocyclic" shall mean an optionally substituted moiety that is cyclic and contains at least one atom other than a carbon atom, such as a nitrogen, sulfur, oxygen or other atom. A heterocyclic ring shall contain up to four atoms other than carbon selected from nitrogen, sulfur and oxygen. These rings may be saturated or have unsaturated bonds. Fused rings are also contemplated by the present invention. A heterocycle according to the present invention is an optionally substituted imidazole, a piperazine (including piperazinone), piperidine, furan, pyrrole, imidazole, thiazole, oxazole or isoxazole group, among numerous others. Depending upon its use in context, a heterocyclic ring may be saturated and/or unsaturated. In instances where a heterocyclic ring is fully unsaturated, there is overlap with the term "heteroaryl".

The term "unsubstituted" shall mean substituted only with hydrogen atoms. The term "substituted" shall mean, within the chemical context of the compound defined, a substituent (each of which substituents may itself be substituted) selected from a hydrocarbyl (which may be substituted itself, preferably with an optionally substituted alkyl or halogen (fluoro) group, among others), preferably an alkyl (generally, no greater than about 12 carbon units in length), an optionally substituted aryl (which also may be heteroaryl and may include an alkylenearyl or alkyleneheteroaryl), an optionally substituted heterocycle (especially including an alkyleneheterocycle), $CF_3$, halogen (especially fluoro), thiol, hydroxyl, carboxyl, oxygen (to form a keto group), $C_1$-$C_8$ alkoxy, CN, nitro, an optionally substituted amine (e.g., an alkyleneamine or a $C_1$-$C_6$ monoalkyl or dialkyl amine), $C_1$-$C_8$ acyl, $C_1$-$C_8$ alkylester, $C_1$-$C_8$ alkyleneacyl (keto), $C_1$-$C_8$ alkylene ester, carboxylic acid, alkylene carboxylic acid, $C_1$-$C_8$ thioester, $C_2$-$C_8$ ether, $C_1$-$C_8$ thioether, amide (amido or carboxamido), substituted amide (especially mono- or di-alkylamide) or alkyleneamide, an optionally substituted carbamate or urethane group, wherein an alkylene group or other carbon group not otherwise specified contains from 1 to 8 carbon units long (alternatively, about 2-6 carbon units long) and the alkyl group on an ester group is from 1 to 8 carbon units long, preferably up to 4 carbon units long. Various optionally substituted moieties may be substituted with 5 or more substituents, preferably no more than 3 substituents and preferably from 1 to 3 substituents.

The term "geometric isomer" shall be used to signify an isomer of a compound according to the present invention wherein a chemical group or atom occupies different spatial positions in relation to double bonds or in saturated ring systems having at least three members in the ring as well as in certain coordination compounds. Thus "cis" and "trans" isomers are geometric isomers as well as isomers of for example, cyclohexane and other cyclic systems. In the present invention all geometric isomers as mixtures (impure) or pure isomers are contemplated by the present invention. In preferred aspects, the present invention is directed to pure geometric isomers.

The term "optical isomer" is used to describe either of two kinds of optically active 3-dimensional isomers (stereoisomers). One kind is represented by mirror-image structures called enantiomers, which result from the presence of one or more asymmetric carbon atoms. The other kind is exemplified by diastereomers, which are not mirror images and which contain at least two asymmetric carbon atoms. Thus, such compounds have $2_n$ optical isomers, where n is the number of asymmetric carbon atoms. In the present invention all optical isomers in impure (i.e., as mixtures) or pure or substantially pure form (such as enantiomerically enriched or as separated diastereomers) are contemplated by the present invention. In certain aspects, the pure enantiomer or diastereomer is the preferred compound.

The present invention includes the compositions comprising the pharmaceutically acceptable salt. i.e., the acid or base addition salts of compounds of the present invention and their derivatives. The acids which may be used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines, among others.

Regardless of the mechanism, the compounds of the present invention may be used to treat disease states or conditions in patients or subjects who suffer from those conditions or disease states or are at risk for those conditions. In this method a compound in an effective amount is administered to a patient in need of therapy to treat the condition(s) or disease state(s). These disease states and conditions include obesity and diabetes and related disease states and conditions which occur associated with these conditions, such as insulin resistance, metabolic syndrome and the like.

Compositions according to the present invention may be administered by any conventional means known in the art. Pharmaceutical formulations include those suitable for oral, rectal, nasal, topical (including buccal and sub-lingual), vaginal or parenteral (including intramuscular, sub-cutaneous and intravenous) administration. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above-described formulations may be adapted to provide sustained release characteristics of the active ingredient(s) in the composition using standard methods well-known in the art.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenous or intramuscular dosage form, as well as via other parenteral routes, such as transdermal, buccal, subcutaneous, suppository or other route, including via inhalation intranasally. Oral dosage forms are preferably administered in tablet or capsule (preferably, hard or soft gelatin) form. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

Compositions suitable for parenteral injection may comprise physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame seed oil, glycerol, tetrahydrofurfuryl alcohol, polyethylene glycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Compositions for rectal or vaginal administration, where applicable, can be prepared by mixing an active agent and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active.

Dosage forms for topical administration include ointments, powders, sprays and inhalants. The compound(s) are admixed under sterile conditions with a physiologically acceptable carrier, and any preservatives, buffers, and/or propellants that may be required. Opthalmic formulations, eye ointments, powders, and solutions are also contemplated as being within the scope of this invention.

Chemical Synthesis

The general procedure for preparation of tetrahydroquinoline derivatives is set forth in U.S. Pat. No. 7,875,721 which can be referred to along with other standard synthetic methods known in the art to synthesize compounds disclosed herein. is incorporated by reference in its entirety herein.

EXAMPLES

1. Selective GPER Activation Protects from Diabetes and Obesity

Biology

Methods used to establish that the present invention may be used effectively to treat metabolic disease states and/or conditions including obesity and diabetes are presented in figures FIG. 1-FIG. 9 .

Introduction

In these studies, the ability of GPER and the GPER-selective agonist G-1 to treat obesity and diabetes is presented. Since the endogenous in vivo ligand estradiol (E2) binds multiple endogenous receptors (including estrogen receptors, ERα, ERβ as well as GPR30/GPER), the current experiments selectively activate GPER with G-1, which shows no binding to ERα or ERβ, in animal models of obesity and diabetes employing both female and male animal models.

Materials and Methods

Ovariectomized Female Model and Diet Induced Obesity Model for Male Mice

For females, an ovariectomized female mouse model, with ovary-intact control animals, fed a regular chow diet, was employed. Loss of the ovaries results in the loss of endogenous estrogenic protection towards metabolic pathophysiology and weight gain, resulting in increased overall weight gain, abdominal adiposity and ensuing metabolic (including glucose and lipid) dysfunction in ovariectomized mice compared to ovary-intact control animals. For males, the model employed involves diet-induced obesity. In the absence of the estrogenic protection as in female mice, male mice fed a high fat chow gain weight and suffer from metabolic pathophysiology compared to mice on normal chow. In both models, following ovariectomy for females or initiation of high fat diet intake for males, mice were allowed to gain weight and develop glucose intolerance, insulin resistance and inflammation for 12 weeks, followed by treatment with vehicle or the GPER-selective agonist G-1 (females: 200 µg, 3 days per week: Mon-Wed-Fri, subcutaneously for 6 weeks and males: 200 µg, 5 days per week: Mon-Fri, subcutaneously for 8 weeks).

Body Weight, Food Intake, Indirect Calorimetry

For measurement of food intake, activity and energy expenditure, mice were placed in metabolic cages. All measurements were obtained using a computer-controlled indirect calorimetry system. Prior to data collection, mice were acclimatized in the chambers for 24 hours, after which data was collected for the subsequent 48 hours, including two complete light cycles (14 h) and two complete dark cycles (10 h). Oxygen consumption ($VO_2$), carbon dioxide production ($VCO_2$), activity and food consumption were measured for 48 hours. The animals had ad libitum access to standard rodent chow or high fat chow and water during the study. To detect ambulatory activity and position, beam breaks in all the three planes, X, Y and Z directions, were utilized to obtain total activity. To calculate oxygen consumption ($VO_2$) and carbon dioxide production ($VCO_2$) were assessed by measuring the gas concentrations at the inlet and outlet of the sealed chambers.

Tissue Weights and H&E Staining

Post euthanasia, tissues (epididymal/perirenal fat, liver) were dissected and weighed. Tibia length was measured after clearing of soft tissue. For H&E staining, at sacrifice, tissues were fixed in buffered formalin for 24 hours and subsequently embedded in paraffin. Tissue sections (5 µm-thick) were stained with Hematoxylin and Eosin.

Glucose Tolerance Test (GTT), Insulin Tolerance Test (ITT), Fasting Glucose and Insulin Measurement Prior to GTT and ITT, mice were fasted for 4 hours and basal glucose (0 min) was measured. Subsequently, mice were intraperitoneally injected with glucose (2 g/kg body weight) or insulin (0.5 U/kg body weight). After the injection, blood glucose was monitored at regular time intervals (15, 30, 60 and 120 min after injection) from tail nicks. Additionally, for measuring the fasting insulin, blood was collected from the tail nicks at 0 time point and plasma was separated and used for measuring the fasting insulin using a mouse Insulin ELISA kit. Blood glucose was monitored using a glucose meter.

Cell Culture

Mouse fibroblasts, NIH 3T3-L1 cells were grown in DMEM with 10% FBS and subcultured before reaching 70% confluence. For differentiation, cells were seeded in 24 well plates or 60 mm dishes and allowed to grow till confluent. Subsequently medium was changed and cells were kept for additional two days before adding the differentiation cocktail in the medium (0.5 mM isomethyl-butylxanthine, 1 µM dexamethasone and 10 µg/mL insulin) for 3 days (with or without GPER selective agonist G-1). The medium was then changed to the regular DMEM with FBS as above.

For human adipocytic differentiation, human preadipocytes were purchased from Zen-Bio and differentiated with or without GPER-selective agonist G-1. Mouse myoblasts, C2C12 were grown in low glucose DMEM with 10% FBS and subcultured before reaching 70-80% confluence. For differentiation into myocytes, cells were seeded on 12-well plates and at confluence were switched to DMEM containing 2% horse serum. The medium was changed every other day and cells were used for glucose uptake assay between 6-8 days post differentiation.

Oil Red O Staining for Neutral Lipids

Eight days after differentiation, adipocytes are briefly rinsed with PBS and fixed in 4% PFA for 30-60 min and washed with PBS. Freshly prepared Oil Red-O working solution was added to cells and incubated for ~60 min at room temperature, washed t 3 times with PBS and air dried. Images were acquired or lipids extracted with isopropanol and absorbance at 520 nm to quantitate the lipids measured.

Glucose Uptake

Differentiated C2C12 cells were washed twice with Krebs-Ringer phosphate buffer and incubated in serum free low glucose DMEM for 3 hours. Cells were then treated with 100 nM insulin for 15 min and subsequently incubated in Krebs-Ringer phosphate buffer containing 0.5 mCi of 2-deoxy-d-[$^3$H]glucose for 20 min. The reaction was terminated by adding ice-cold PBS on plates on ice. After three washes with PBS, the cells were dissolved in 0.1% sodium dodecyl sulfate and radioactivity was quantified by liquid scintillation counting. Nonspecific deoxyglucose uptake was measured in the presence of 20 mM cytochalasin B and was subtracted from the total uptake to get specific glucose uptake.

Real-Time Quantitative PCR Analysis

Total RNA was extracted from frozen tissues (~100 mg) or cultured cells using the RNeasy Mini Kit. Isolated RNA (~100 ng) was used for cDNA synthesis using the ImProm-II™ Reverse Transcription System in a final reaction volume of 20 µL in a denaturation and extension cycle. Subsequently, quantitative real time PCR was carried out in a 7500 Fast Real-Time PCR System. Gene expression was normalized to 18S RNA as an internal reference and fold change over the control was calculated using the ddCt method. Quantitative real-time PCR analyses were performed in triplicate from a minimum of 5 separate animals.

Western Blotting

Tissues were homogenized in RIPA buffer supplemented with sodium fluoride (50 mM), sodium orthovanadate (1 mM), phenylmethylsulfonylfluoride (1 mM), and protease cocktail. Protein amounts were quantified by Bradford method and equal amounts (30 µg) of protein were loaded for all the samples on 4-20% SDS-PAGE gel. Proteins were then transferred to polyvinylidene fluoride membrane, blocked with 3% newborn calf serum in TBST before overnight incubation with primary antibodies. Subsequently, blots were incubated with secondary HRP-conjugated antibodies and developed using SuperSignal West Pico Chemiluminescent Substrate. Blots were then scanned and quantified using ImageJ software.

Statistical Analysis

For every experiment, data were pooled from a minimum of 4-8 mice or at least 3 independent experiments. Significance was determined by Student's t-test or one-way ANOVA with appropriate post-hoc analyses using GraphPad Prism (GraphPad Software). P values of <0.05 were considered significant.

Results

Mice were weighed periodically during the treatment and as shown in FIG. 1, treatment of both females and males with G-1 resulted in a decrease in the total body weight compared to the vehicle-treated animals. To investigate the source of relative weight loss, food intake and energy expenditure (the amount of $O_2$ consumed) were measured in metabolic cages. Although there was no change in food intake in the treated vs. untreated groups (data not shown), an increase in $O_2$ consumption in the G-1-treated mice (both males and females) was observed (FIG. 2), suggesting that G-1 increases metabolism in vivo.

Since both animal models resulted in metabolic dysfunction as revealed by higher fasting glucose levels (FIGS. 3A & 3B), the effect of G-1 treatment on glucose tolerance and insulin sensitivity was determined. The results revealed that treatment of both female and male mice with G-1 resulted in improved glucose tolerance as well as lower fasting glucose levels in vivo (FIGS. 3A & 3B). Furthermore, male mice on a high fat diet demonstrated improved insulin sensitivity upon G-1 treatment (FIG. 3B). Taken together these results demonstrate that G-1 treatment of ovariectomized female mice and male mice fed high fat chow improves glucose metabolism, reflecting an anti-diabetic effect.

Following the 6-8 week treatment with G-1, mice were terminally sacrificed and individual tissues were dissected and weighed. In female mice, G-1 treatment resulted in decreased weights of perigonadal fat pads (FIG. 4A). However, G-1 treatment of male mice resulted in a significant decrease in liver weights as well as perirenal adipose fat pad weights (FIG. 4B). Furthermore, histology of female perigonadal fat pads by hematoxylin and eosin staining revealed smaller adipocytes in the G-1 treated mice (FIG. 4A).

Figure 5:
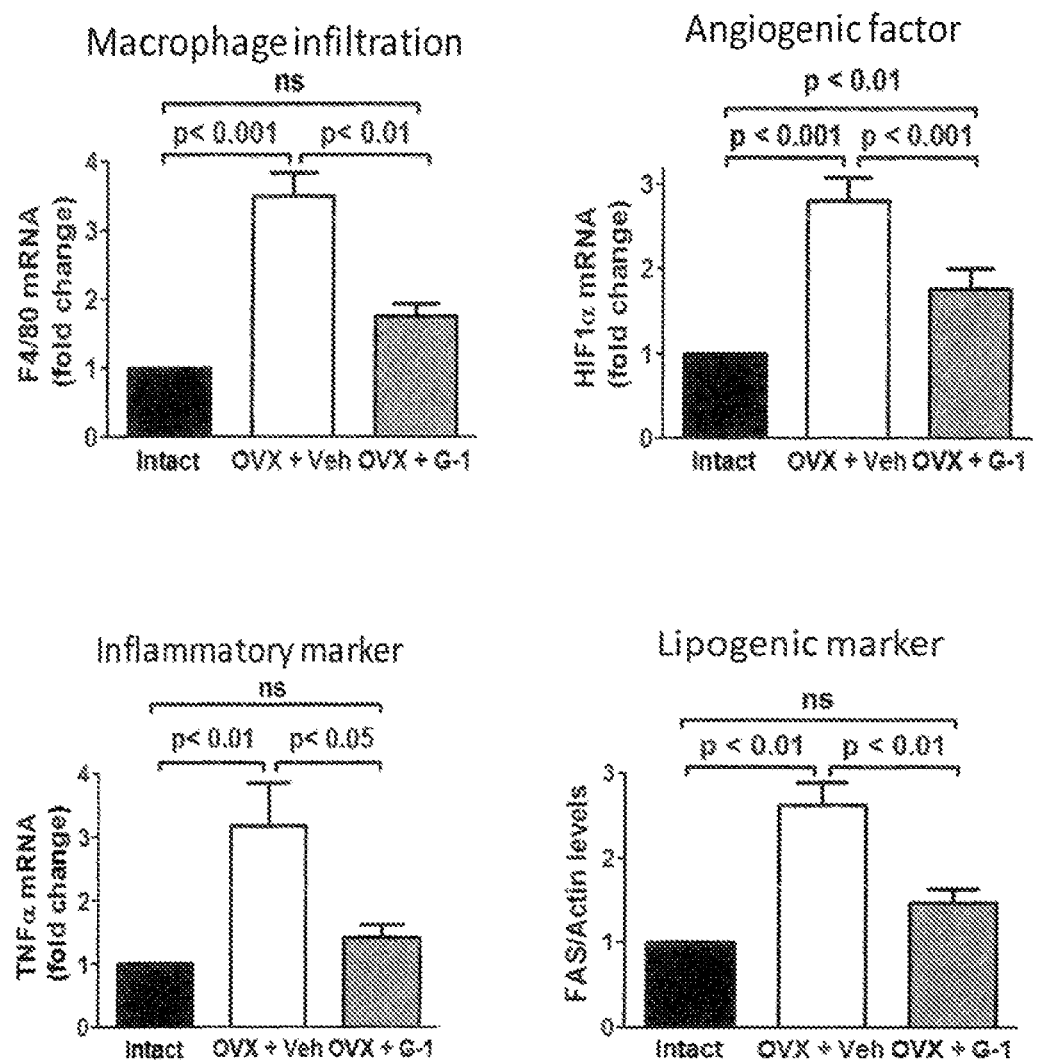
FIG. 5 shows that G-1 treatment in ovariectomized females reduces inflammatory, angiogenic and lipogenic markers in gonadal fat.
Figure 6:
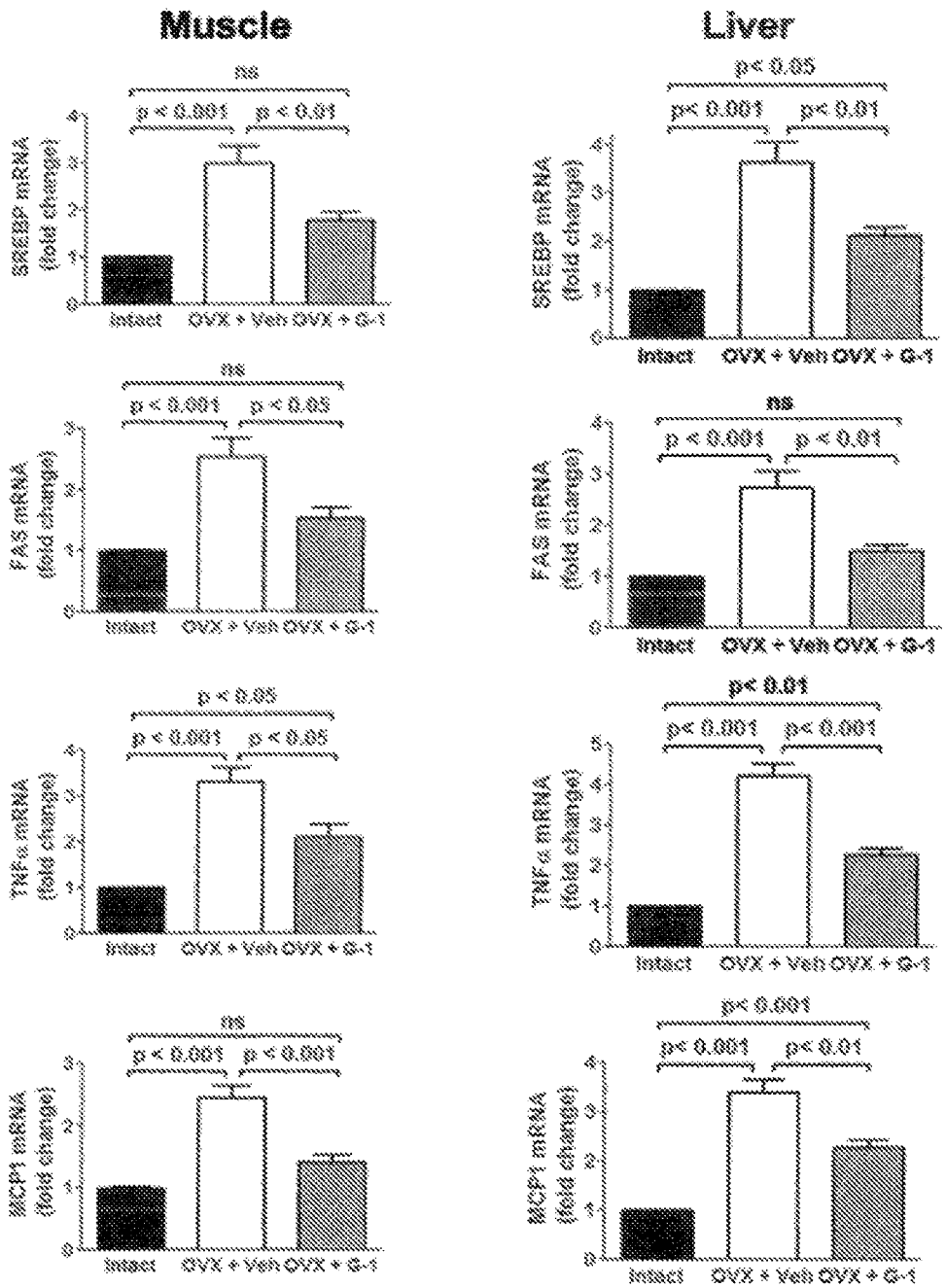
FIG. 6 shows that treatment with G-1 in ovariectomized females reduces lipogenic and inflammation and increases antioxidant markers in muscle and liver.

Changes in inflammatory, angiogenic and lipogenic markers of tissues harvested from the G-1-treated mice were compared to control mice by quantitative PCR. mRNA levels of representative pro-inflammatory, angiogenic and lipogenic markers were lower in the adipose tissue of G-1-treated mice (FIG. 5). In addition, skeletal muscle and liver exhibited decreased pro-inflammatory and lipogenic markers (FIG. 6). These results demonstrate that G-1 treatment remodels multiple tissues towards a state of decreased fat deposition and reduced inflammation.

Figure 7:
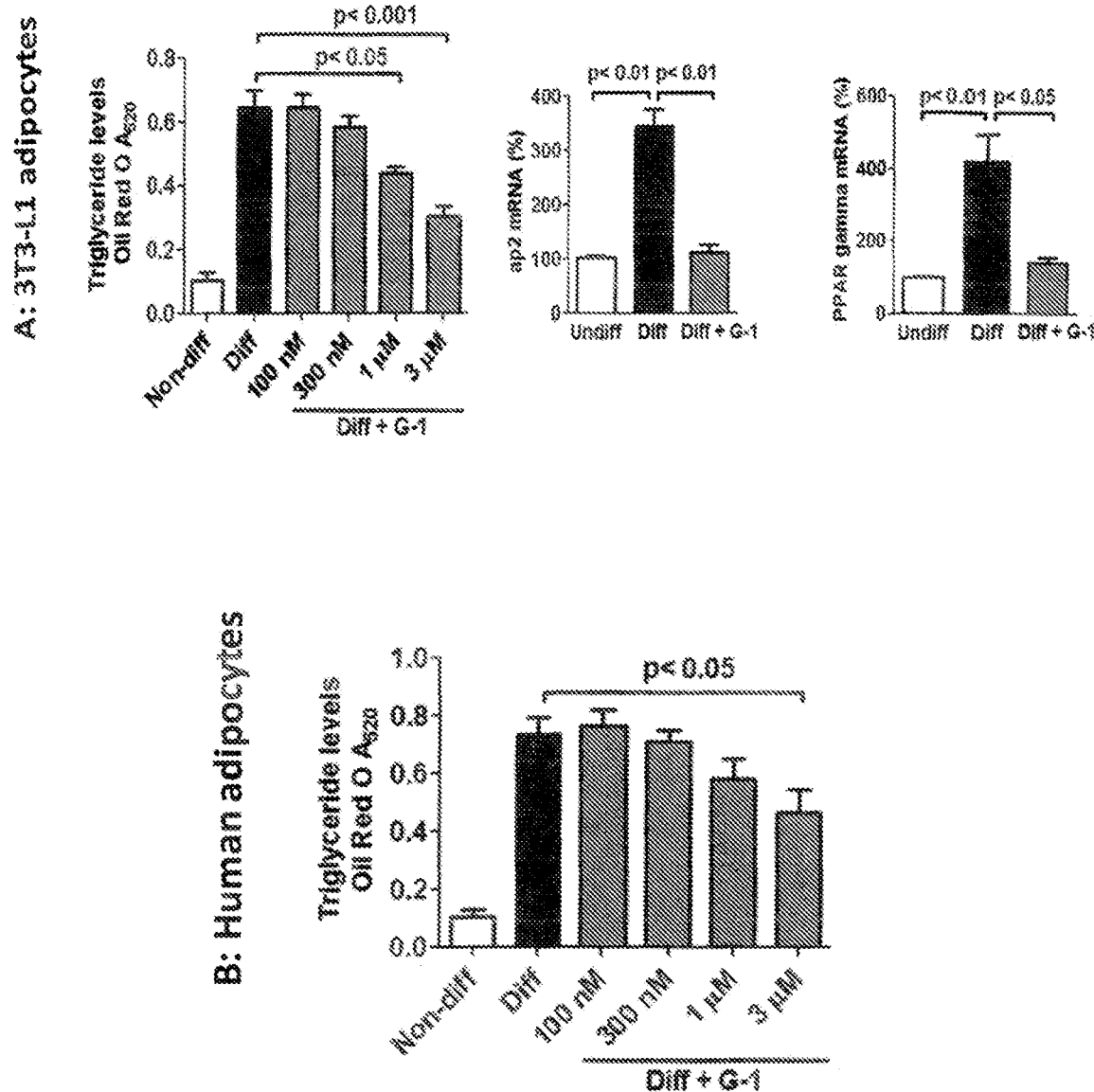
FIG. 7 shows that G-1 treatment inhibits lipid accumulation in 3T3-L1 murine and human adipocytes (A & B) and down regulates the expression of adipogenic markers ap2 and PPAR gamma in adipocytes (A).

To further understand the mechanism of G-1 action and corroborate the above results at the cellular level, adipocyte (3T3-L1/human) and myocyte (C2C12) cell lines were employed. Treatment of murine as well as human adipocytes with GPER-selective agonist G-1 during differentiation resulted in decreased lipid accumulation as revealed by Oil Red O staining (FIG. 7). Furthermore, 3T3-L1 cells differentiated in the presence of G-1 also expressed lower levels of adipogenic markers such as PPARγ and ap2 (also known as fatty acid binding protein 4) (FIG. 7), further extending the results from animal studies that G-1 treatment prevents lipid accumulation.

Figure 8:
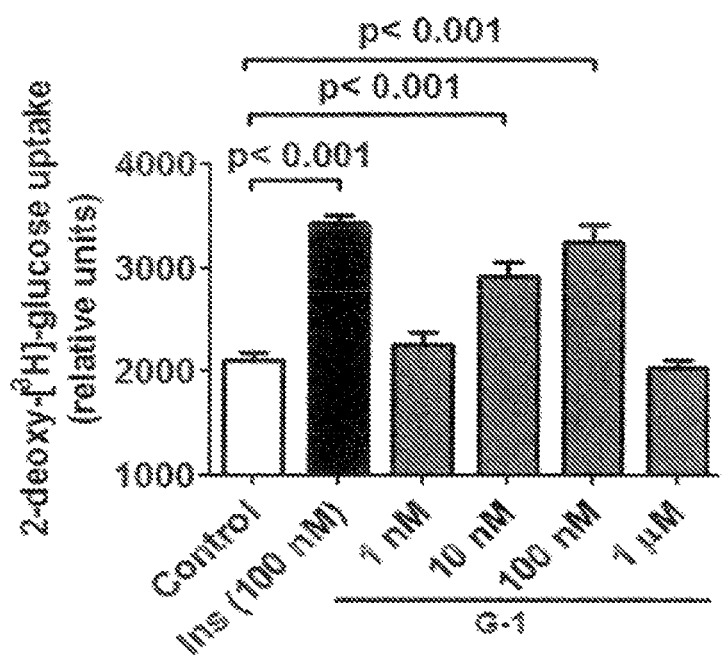
FIG. 8 shows that G-1 treatment increases glucose uptake in differentiated C2C12 myocytes.

Differentiated murine myocytes (C2C12 cells) represent a widely used cellular model of glucose uptake. G-1 treatment increased the cellular uptake of glucose in myocytes (FIG. 8). This result indicates that in vivo, G-1 likely increases glucose uptake in metabolically active tissues such as skeletal muscle, which may result in the improved insulin sensitivity and improved glucose tolerance observed in in vivo studies.

Figure 9:
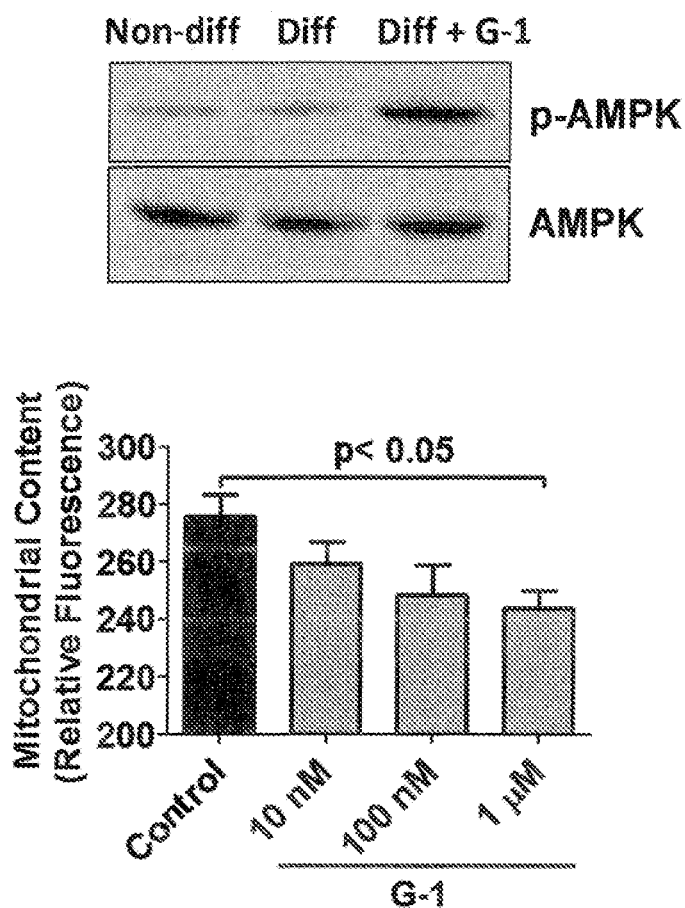
FIG. 9 shows that the GPER agonist G-1 activates AMPK and increases mitochondrial biogenesis in differentiated murine adipocytes.
Figure 10:
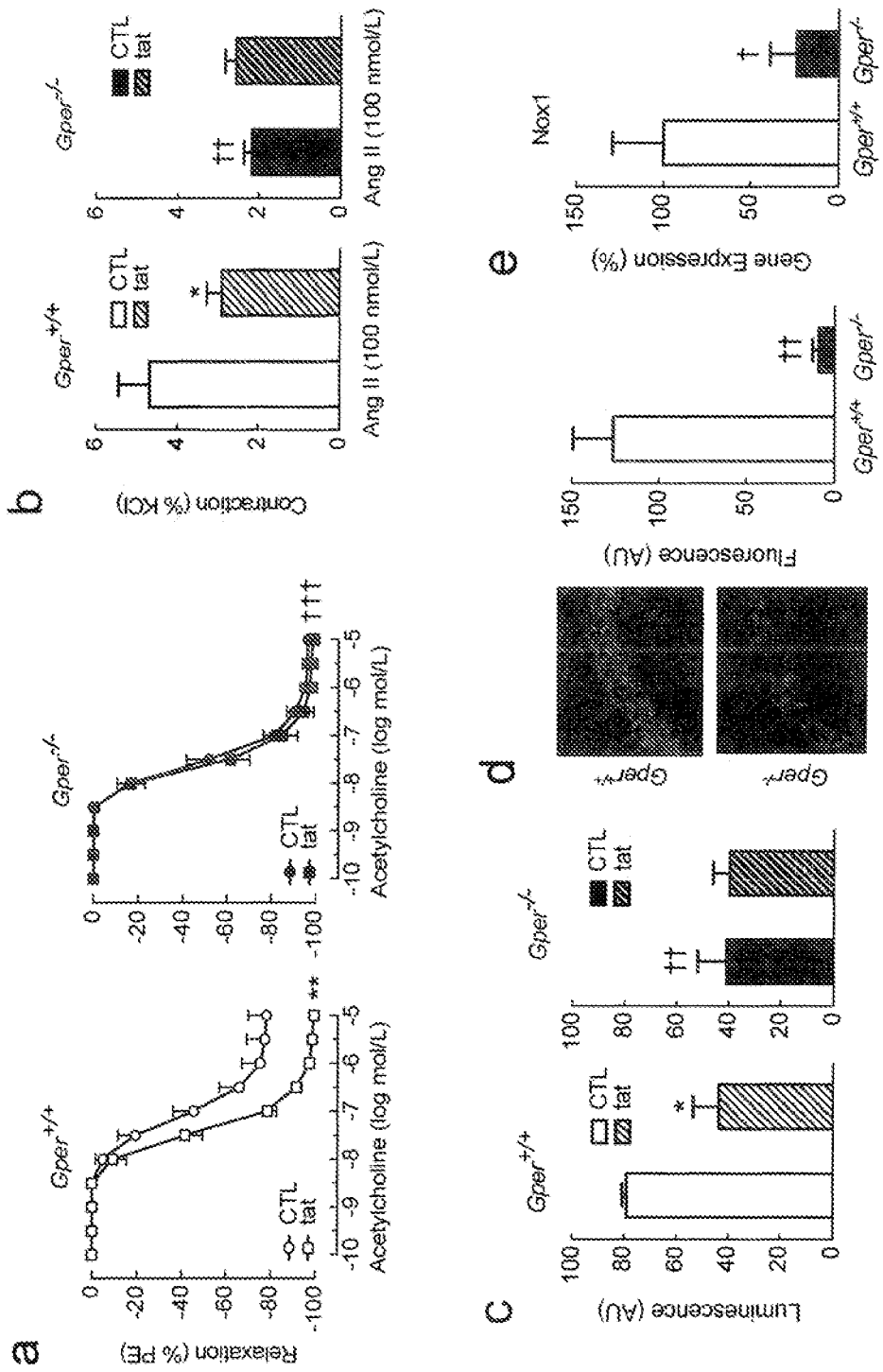
FIG. 10 shows that Gper deletion inhibits cardiovascular oxidative stress and Nox1 expression in aged mice. Nox-dependent vascular reactivity (a, b), vascular superoxide production as detected by chemiluminescence (c) or DHE fluorescence (d, f), nitrotyrosine staining as a molecular marker of oxidative stress (g), and Nox1 gene expression (e, h) in arteries (a-e) and ventricular myocardium (f-h) of aged $Gper^{-/-}$ (closed bars) compared with aged wild-type Gper mice (open bars). Subsets of arteries were treated with the Nox-selective inhibitor gp91ds-tat (tat, hatched bars) as indicated. Endothelium-dependent, NO-mediated vasodilation in response to acetylcholine is impaired in aged $Gper^{+/+}$ mice, which is completely mediated by increased Nox activity, while vasodilation is preserved in aged $Gper^{-/-}$ mice (a). As with NO-dependent vasodilation, arterial contractions to Ang II in aged $Gper^{+/+}$ mice involve Nox-dependent pathways, an effect which is completely abolished in $Gper^{-/-}$ mice (b). Importantly, Gper deletion only abrogates Nox-dependent, but not Nox-independent vascular superoxide production (c, d). Consistent with these findings, vascular Nox1 gene expression (e) is markedly reduced in mice lacking GPER. Deletion of GPER also markedly suppresses myocardial superoxide-derived oxidative stress (f, g) and Nox1 expression (h) in aged mice. All data (n=3-10) are mean±s.e.m. *P<0.05, **P<0.01 vs. control (CTL); †P<0.05, ††P<0.01, †††P<0.001 vs. $Gper^{+/+}$ (ANOVA with Bonferroni post-hoc tests in a-c; Student's t-test in d-h).
Figure 10:
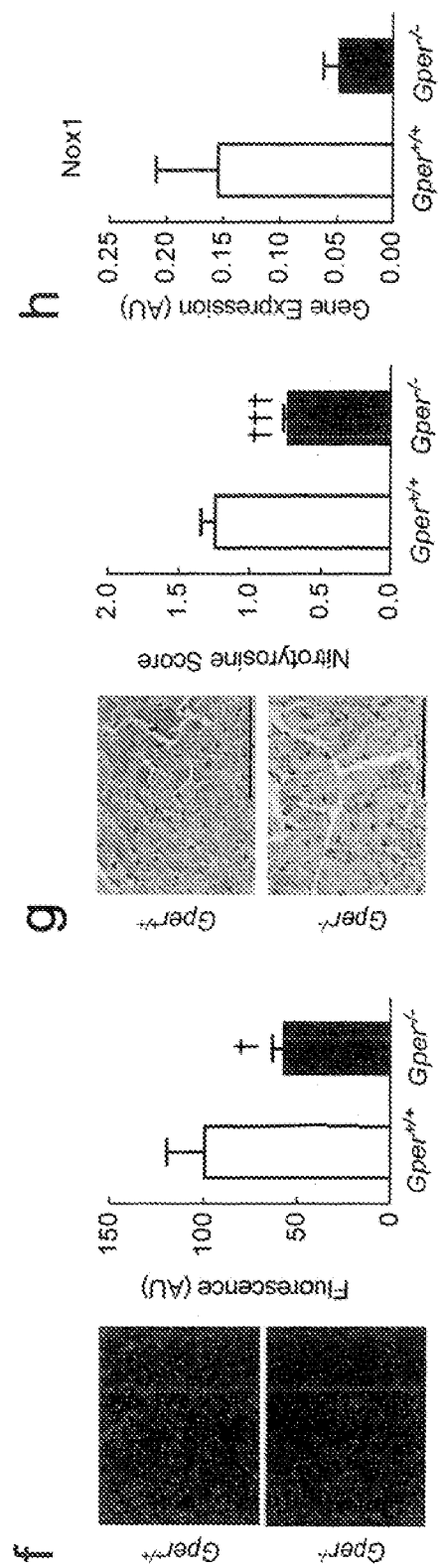
Figure 11:
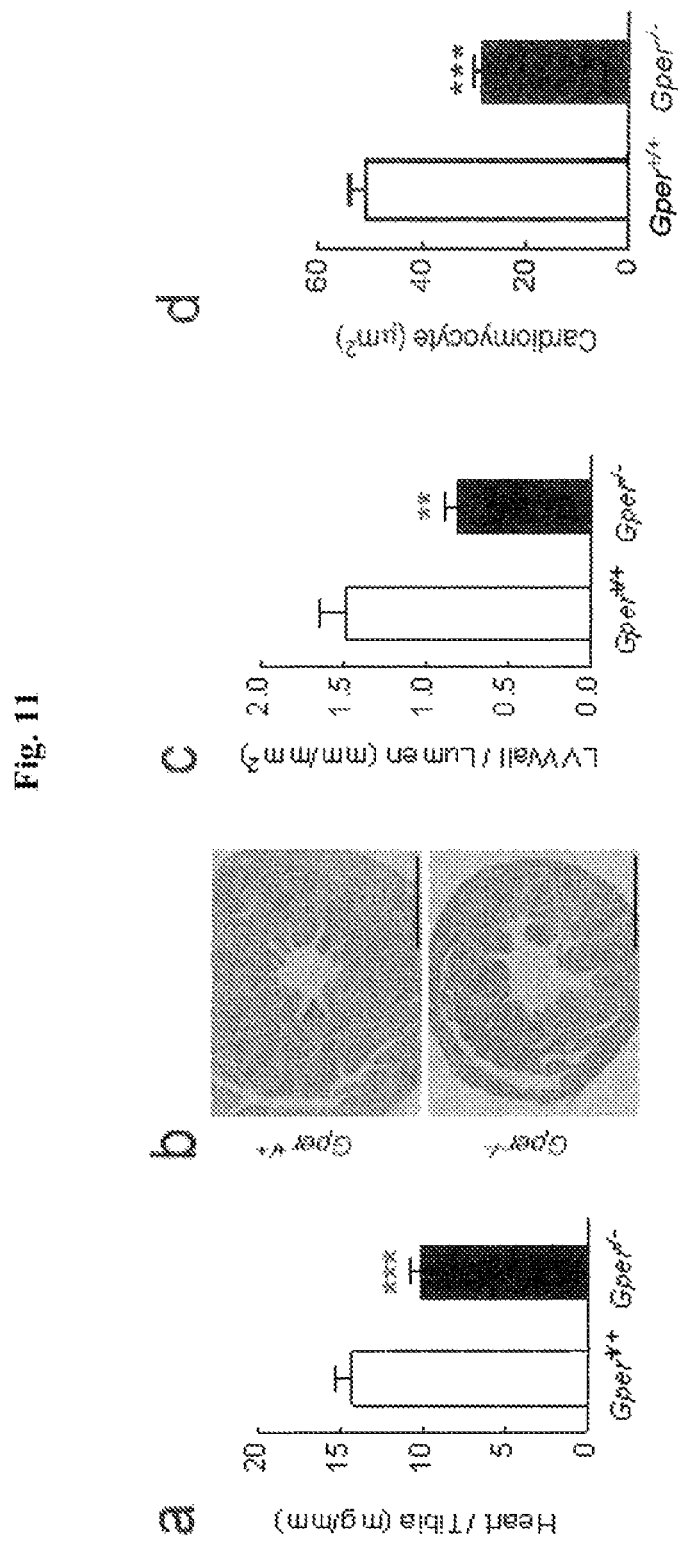
FIG. 11 shows the essential role of GPER as a determinant of left ventricular hypertrophy, fibrosis, and diastolic dysfunction in the aging heart. Total heart weights (a), histologic myocardial changes (b-g), as well as dimensions and function of the left ventricle determined by echocardiography (h j) in aged (24 month-old) $Gper^{+/+}$ (open bars) and $Gper^{-/-}$ (closed bars) mice. In aged mice, deletion of Gper was associated with lower heart weight (relative to tibial length, a) and inhibition of left ventricular hypertrophy as measured by left ventricular wall to lumen ratio in cross sections (b-c) and cardiomyocyte size ($\mu m^2$) (d). Compared with aged $Gper^{+/+}$ mice, interstitial fibrosis (Sirius red staining, e-f) and collagen type IV content (g) is greatly reduced in $Gper^{-/-}$ mice. The absence of left ventricular hypertrophy in aged $Gper^{-/-}$ mice was further confirmed by M-mode echocardiography (representative parasternal images, h), which also revealed improved diastolic function as determined by early diastolic mitral valve annular velocity (E', i) and myocardial performance index (MPI, j) in $Gper^{-/-}$ mice. All data (n=3-18 per group) are mean± s.e.m. *P<0.05, P<0.01, *P<0.001 vs. $Gper^{+/+}$ mice (Student's t-test).
Figure 11:
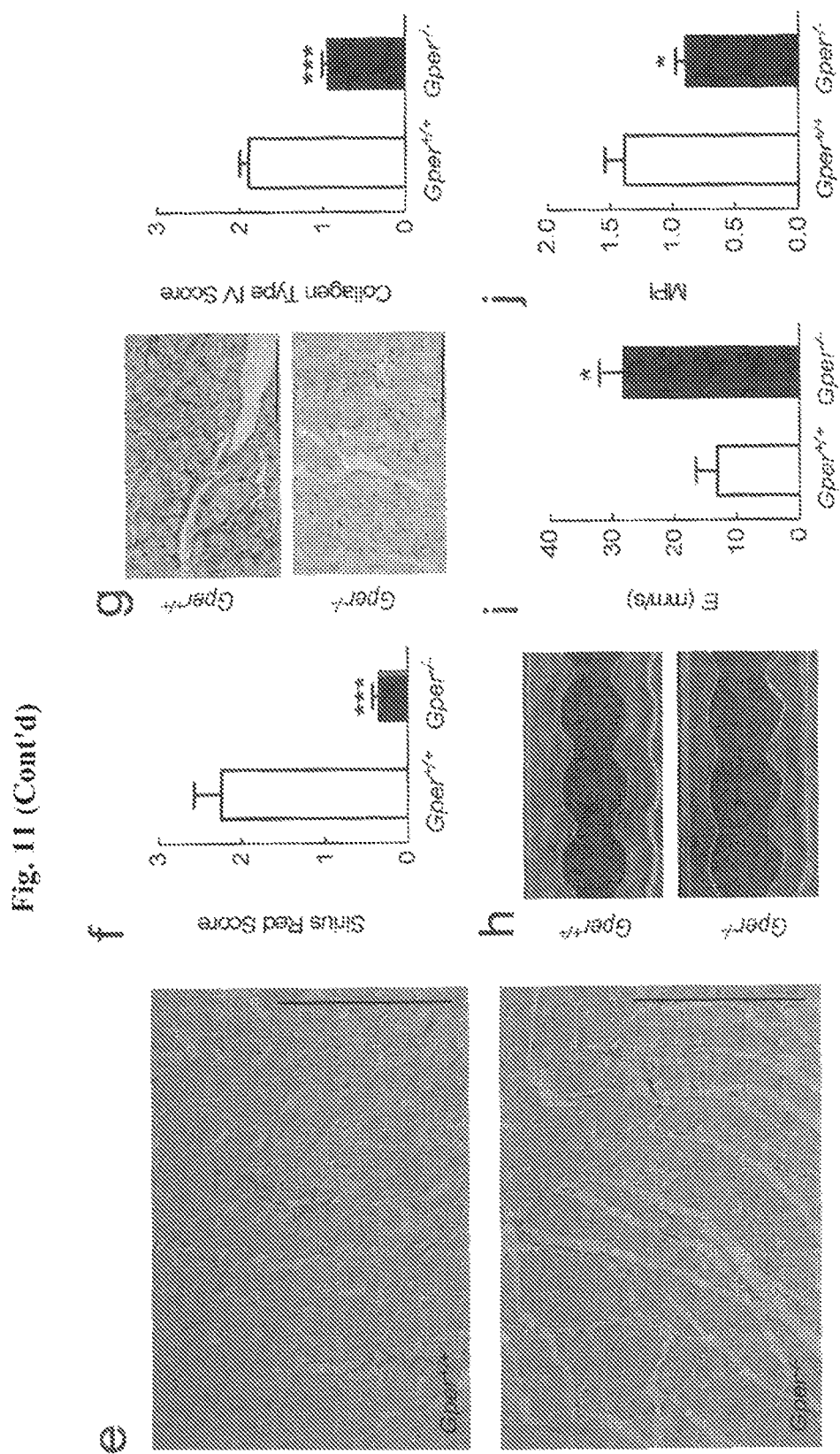
Figure 12:
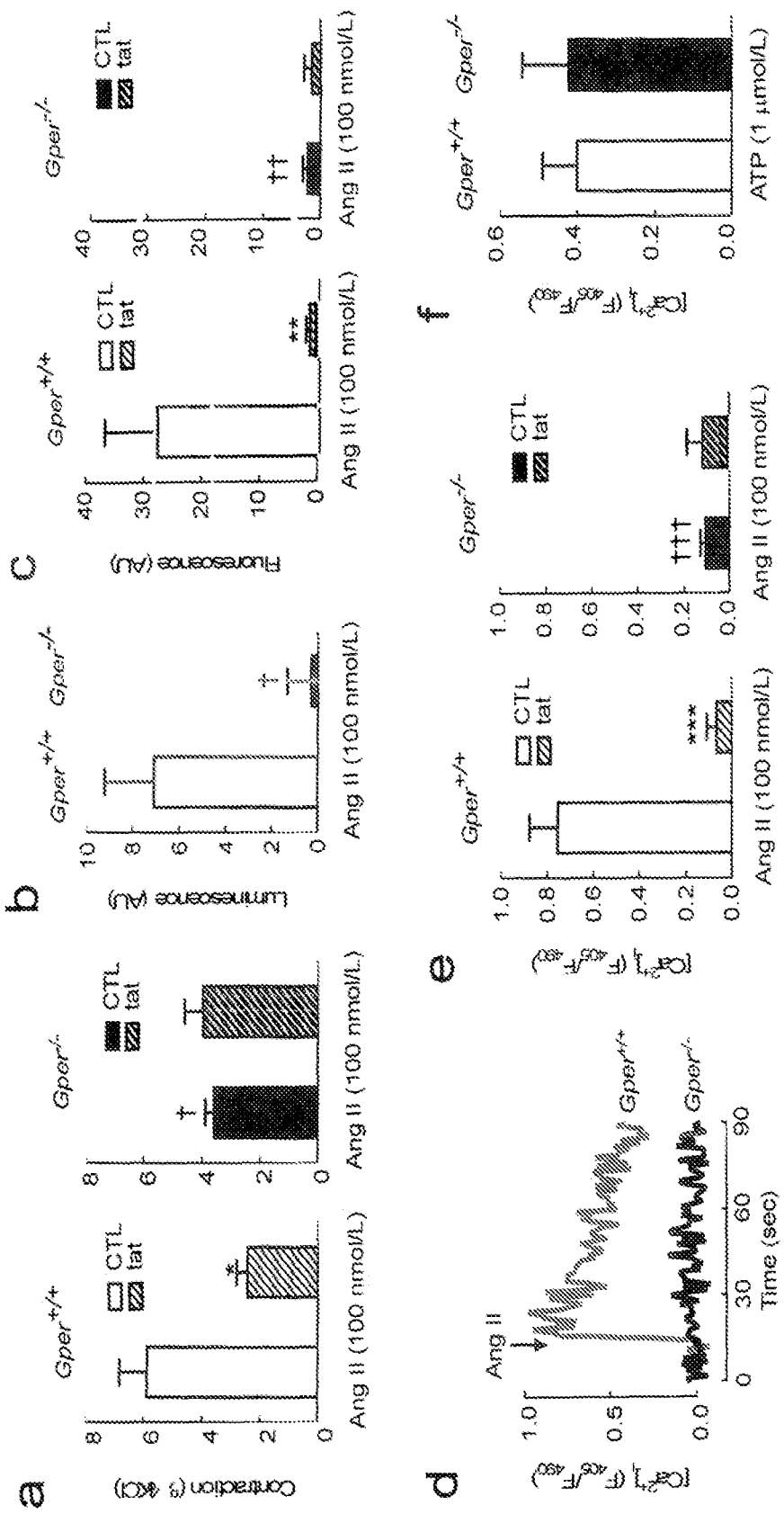
FIG. 12 shows that Gper deletion abolishes vascular Nox activation by Ang II. Ang II was utilized as a prototypic stimulus of Nox activity in mouse arteries and VSMC isolated from young (4 month old) $Gper^{+/+}$ (open bars) and $Gper^{-/-}$ (closed bars) mice. Ang II-induced contractions (a), superoxide production detected by chemiluminescence (b) and DHE fluorescence (c), and intracellular calcium mobilization ([$Ca^{2+}$]$_i$, given as ratio of emitted light at 405 nm and 490 nm, d-f) are shown for intact aortic rings (a) and VSMC (b-f) treated with the Nox-selective inhibitor gp91ds-tat (tat, hatched bars) as indicated. Nox inhibition reduces Ang II-induced vasoconstriction by 58%. Contractions to Ang II were similarly reduced in Gper$^{-/-}$ mice, the residual portion of contraction being unaffected by Nox inhibition (a). In VSMC, Nox-dependent superoxide formation in response to Ang II is completely absent in cells derived from Gper$^{-/-}$ mice and fully blocked by Nox inhibition (b-c). Similarly, Nox-dependent intracellular Ca$^{2+}$ mobilization in response to Ang II is absent in Gper$^{-/-}$ mice (original recording, d, and cumulative data, e), whereas ATP-induced Ca$^{2+}$ mobilization is unaffected by Gper deletion (f). All data (n=3-12) are mean±s.e.m. *P<0.05, P<0.01, *P<0.001 vs. control (CTL); †P<0.05, ††P<0.01, †††P<0.001 vs. Gper$^{+/+}$ (ANOVA with Bonferroni post-hoc tests in a, c and e; Student's t-test in b).

Further studies on differentiated murine adipocytes revealed that G-1 treatment activated AMP-activated protein kinase (AMPK) (FIG. 9), an important enzyme that plays a role in cellular energy homeostasis. Furthermore, treatment with G-1 increased the mitochondrial biogenesis (FIG. 9). Increases in AMPK activation and mitochondrial biogenesis indicate higher metabolism in metabolically active tissues that may result in improved insulin sensitivity and glucose tolerance with a concomitant decrease in body weight.

Conclusions

Overall, these results demonstrate that GPER and the GPER-selective agonist G-1 mediate multiple metabolic cellular events that culminate in the regulation of metabolism and both glucose and lipid metabolism, resulting in weight reduction and improved glucose homeostasis in vivo, suggesting novel therapeutic agents and mechanisms for the treatment of obesity and diabetes.

2. GPER Deficiency and Selective Inhibition Protect from Cardiovascular Aging via Reactive Oxygen Species (ROS) Biology Methods used to establish that the present invention may be used effectively to treat disease states and/or conditions that are mediated through reactive oxygen species through excessive formation of reactive oxygen species are presented in figures FIG. 10-FIG. 13 and Suppl. FIG. 15-FIG. 20.

Materials and Methods

Study Design

The aim of these studies was to explore whether and through which mechanisms GPER regulates cardiovascular oxidative stress induced by aging or Ang II. For this purpose, we used wild-type and Gper-deficient mice in a model of aging, as well as mice chronically infused with Ang II. In addition, the small molecule GPER antagonist G36 was employed to test the capability of modulating oxidative stress by pharmacological targeting of GPER. Detailed mechanistic studies were carried out in primary vascular smooth muscle cells (VSMC) isolated from wild-type and Gper$^{-/-}$ mice, as well as in human VSMC.

Mice and Aging Model

Male Gper$^{-/-}$ mice were generated and backcrossed 10 generations onto the C57BL/6 background (Harlan Laboratories) as described. Wild-type C57BL/6 and Gper$^{-/-}$ littermates were housed under controlled temperature of 22-23° C. on a 12 h light-dark cycle with unrestricted access to standard chow and water. Mice aged 24 months were used as a model of aging, which closely resembles functional and structural changes of human cardiovascular aging. Animals were euthanized at the age of 4, 12 or 24 months by intraperitoneal injection of sodium pentobarbital (2.2 mg g$^{-1}$ body weight).

Ang II-Induced Hypertension Model

Micro-osmotic pumps (Alzet model 1002, Durect) were implanted subcutaneously in the midscapular region of wild-type and Gper$^{-/-}$ mice under isoflurane (3%) anesthesia. Pumps continuously delivered PBS or Ang II (MP Biomedicals) at a rate of 0.7 mg kg$^{-1}$ per day for 14 days. Three days prior to pump implantation, pellets continuously releasing the GPER-selective antagonist G36 (33 µg per day, Innovative Research of America) or placebo were implanted subcutaneously into the right hindlimb of selected wild-type mice.

Vascular Smooth Muscle Cells

Primary aortic VSMCs from wild-type and Gper$^{-/-}$ mice (n=10 per genotype) were isolated and cultured. Human aortic VSMC (Lonza) were cultured according to the provider's recommendations. Experiments were performed with cells derived from passages 2 to 5 for murine and 2 to 8 for human VSMC. For functional assays, cells at subconfluence were rendered quiescent by overnight serum starvation.

Measurement of Superoxide ($O_2^-$) by Lucigenin-Enhanced Chemiluminescence

Following euthanization, the aorta was immediately excised, carefully cleaned from perivascular adipose and connective tissue, opened longitudinally, and cut into segments of identical size (3 mm) in cold (4° C.) physiological saline solution. Tissues were transferred and equilibrated in HEPES-buffer in a humidified incubator at 37° C. for 60 min. In addition to intact isolated arteries, vascular smooth muscle cells (VSMCs) and a cell free $.O_2^-$ generating system generated by adding the substrate xanthine (100 µmol L$^{-1}$, Calbiochem) to xanthine oxidase (0.05 mU, Calbiochem) were employed. Chemiluminescence was measured in dark-adapted buffer containing 5 µmol L$^{-1}$ lucigenin (Enzo Life Sciences) at 37° C. After equilibrating for 15 min, $.O_2^-$ production was induced by Ang II (100 nmol L$^{-1}$). Where indicated, tissues or cells were pretreated with the Nox-selective inhibitor gp91ds-tat (Anaspec, 3 µmol L$^{-1}$), the GPER-selective antagonist G36 (10 nmol L$^{-1}$, 100 nmol L$^{-1}$, or 1 µmol L$^{-1}$), the $.O_2^-$ dismutase mimetic tempol (100 µmol L$^-$, Tocris Bioscience), or vehicle control (DMSO 0.01%). Luminescence was measured 10-times in 20 sec intervals using a Synergy H1 multi-mode microplate reader (BioTek), and readings were averaged to reduce variability. A background reading was subtracted, and $.O_2^-$ production normalized to surface area of vascular segments or to VSMC number, respectively.

In Situ Detection of $.O_2^-$ by Dihydroethidium (DHE)

The thoracic aorta was equilibrated in a humidified incubator at 37° C. for 60 min, and treated with the Nox-selective inhibitor gp91ds-tat (3 µmol L$^{-1}$) for 30 min when indicated. Tissues were frozen in optimum cutting temperature (O.C.T.) compound (Sakura Finetek), cut on a cryostat into 10 µm thick sections, and stored on glass slides at −80° C. For staining, sections were incubated with DHE (5 µmol L$^{-1}$, Invitrogen) in HEPES-PSS for 15 min at room temperature in the dark. In separate experiments, VSMC were grown on poly-L lysine coated coverslips, which were incubated with DHE (5 µmol L$^{-1}$) in HEPES-PSS for 30 min at 37° C. in the dark. Where indicated, VSMC were pretreated with Nox-selective inhibitor gp91ds-tat (3 µmol L$^{-1}$) for 30 min, and $.O_2^-$ production was stimulated by Ang II (100 nmol L$^{-1}$) for 20 min prior to imaging. Slides with VSMC or aortic sections were carefully washed, mounted in buffer with coverslips, and immediately imaged by epifluorescence microscopy (Axiovert 200M, Zeiss) using a rhodamine filter with exposure intensity adjusted to background fluorescence. Signal intensity was quantified using ImageJ software (National Institutes of Health).

Vascular Reactivity Studies

The aorta was immediately excised after euthanization, carefully cleaned from perivascular adipose and connective tissue and cut into 2 mm long rings in cold (4° C.) buffer. Aortic rings were mounted in myograph chambers (multi-channel myograph system 620M, Danish Myo Technology) onto 200 µm pins. A PowerLab 8/35 data acquisition system and LabChart Pro software (AD Instruments) were used for recording of isometric tension. Experiments to determine vascular reactivity of aortic rings were performed as described. Briefly, rings were equilibrated in buffer (37° C.; pH 7.4; oxygenated with 21% $O_2$, 5% $CO_2$, and balanced $N_2$) for 30 min and stretched step-wise to the optimal level of passive tension for force generation. Functional integrity of vascular smooth muscle was confirmed by repeated exposure to KCl, with resulting contractions demonstrating no differences between groups. Selected arteries were pretreated with the Nox-selective inhibitor gp91ds-tat (3 µmol L$^{-1}$) for 30 min. Contractions to Ang II (100 nmol L$^{-1}$) were studied in the abdominal aorta in the presence of the NO synthase inhibitor L-N$^G$-nitroarginine methyl ester (L-NAME, 300 µmol L$^{-1}$, incubation for 30 min, Cayman Chemical) to exclude Ang II-mediated release of NO. Ang II-induced contractions exhibit rapid desensitization in the mouse vasculature with a nearly complete loss of tension after about 2 min, thus preventing the recording of responses to increasing concentrations. To study endothelium-dependent, NO-mediated relaxations, rings from the thoracic aorta were precontracted with phenylephrine to 80% of KCl-induced contractions, and responses to acetylcholine (0.1 nmol L$^{-1}$-10 µmol L$^{-1}$) were recorded. Precontraction did not differ between groups. To exclude any GPER-dependent effects on vasoconstrictor prostanoids, responses were obtained in the presence of the cyclooxygenase-inhibitor meclofenamate (1 µmol L$^{-1}$, incubation for 30 min,). Contractions were calculated as the percentage of contraction to KCl, and relaxation is expressed as the percentage of precontraction to phenylephrine.

Cardiac Histology

After sacrifice, hearts were excised, fixed in 4% paraformaldehyde and embedded into paraffin blocks. Histological sections (2 µm) were stained with hematoxylin-eosin, Sirius Red or by immunohistochemistry using polyclonal goat anti-collagen IV antibody. Morphometric analysis of free left ventricle wall thickness and ventricular lumen area was performed using light microscopy at 400-fold magnification and cellSens software (Olympus), with left ventricular wall thickness based on analysis of 10 randomly selected measure points. Cardiomyocyte cross-sectional area was determined by analysis of 15 anterolaterally located cardiomyocytes using cellSens software. Myocardial fibrosis on Sirius Red or collagen type IV stained paraffin sections was graded using a semi-quantitative fibrosis score (0=no staining; 1=less than 25%; 2=26-50%; 3=51-75%; 4=more than 75% of cardiac tissue with positive staining). For each heart, the mean score evaluated on 10 power fields at 200-fold magnification was calculated.

High-Resolution, High Frequency Echocardiography

Mice were sedated using light inhaled isoflurane anesthesia and placed on a heat-pad to maintain body temperature, and echocardiography was performed using a Vevo® LAZR photoacoustic imaging system (VisualSonics) using high-resolution, high-frequency ultrasound at 40 mHz. Conventional B-mode, M-mode, pulsed wave- and tissue-doppler images were acquired by an experienced, blinded operator to ensure a standardized, highly consistent technique, and left ventricular dimensions and diastolic function were quantified. Left ventricular ejection fraction was determined by speckle-tracking based wall motion analysis using VevoStrain software (VisualSonics).

Measurement of Arterial Blood Pressure

Systolic blood pressure was measured in conscious mice using a volume-pressure recording noninvasive monitoring system (CODA-6, Kent Scientific).

Intracellular Calcium Mobilization

VSMC were loaded with 5 µmol L$^{-1}$ indol-AM and 0.05% pluronic F-127 in buffer for 30 min at room temperature in the dark. Cells were washed and resuspended (10$^6$ cells per mL), and calcium mobilization in response to Ang II (100 nmol L$^{-1}$) and adenosine triphosphate (ATP, 1 µmol L$^{-1}$) was determined ratiometrically using $\square_{ex}$ 340 nm and $\square_{em}$ 405/490 nm at 37° C. in a QM-2000-2 spectrofluorometer (Photon Technology International).

VSMC Transfection with Nox1 Adenovirus or GPER-Targeted siRNA

VSMC from Gper$^{-/-}$ mice were plated at ~600,000 cells per T25 flask, washed in PBS, and infected with Nox1GFP and GFP control adenovirus constructs at 400 MOI overnight in low serum (1% FBS) DMEM. Cells were allowed to recover for 48 h prior to experiments. Transduction efficiency was determined by GFP expression. For siRNA, human aortic VSMC were transfected with specific 200 pM siGPER supplemented with lipofectamine 2000 for 6-8 h in serum-free media, washed, and returned to normal media. Subsequent experiments were performed 72 h after transfection.

Quantification of Gene and Protein Expression

RNA was extracted, reverse-transcribed and analyzed using SYBR Green-based detection of amplified gene-specific cDNA fragments by qPCR with mouse GAPDH (GenBank ID: NM_008084.2) serving as the house-keeping control. For determination of protein expression by Western blot, VSMC were lysed in NP-40 buffer supplemented with protease inhibitor, 10% SDS, 0.5% sodium fluoride, and 0.5% sodium orthovanadate. 20 or 40 $\square$g of lysate were loaded on 10% SDS-PAGE gel, blotted onto polyvinylidene fluoride membrane, and blocked with 3% newborn calf serum in Tris-buffered saline with Tween-20 (0.1%). Blots were incubated with primary antibodies overnight at 4° C., washed, incubated with secondary HRP-conjugated antibodies (1:5000) for 1 h at room temperature, and developed with Super Signal West Pico Chemiluminescent substrate. Blots were imaged and quantified using ImageJ densitometry analysis software.

Immunofluorescence of Nox1 and GPER

Aortic sections frozen in O.C.T. compound were fixed in 4% paraformaldehyde, blocked and permeabilized in buffer containing normal goat serum (3%) and TritonX-100 (0.01%). Sections were incubated with rabbit anti-mouse Nox1 antibody (1:100, Sigma-Aldrich) or negative control IgG (1:100) overnight at 4° C., washed, incubated with goat anti-rabbit IgG conjugated to Alexa Fluor 488 for one hour, washed, mounted in Vectashield, and imaged utilizing a Leica SP5 confocal microscope. Signal intensity was quantified using ImageJ software. VSMC were stained with a rabbit anti-mouse GPER antibody.

Statistical Analysis

Statistical analysis for in vitro and in vivo experiments was performed using GraphPad Prism version 5.0 for Macintosh (GraphPad Software). When comparing two groups, the two-tailed, unpaired Student's t-test was performed. When comparing various groups, data were analyzed by one- or two-way analysis of variance (ANOVA) followed by Bonferroni's post-hoc test to correct for multiple comparisons. Values are expressed as mean±s.e.m.; n equals the number of animals or cell preparations used. Statistical significance was accepted at a P value<0.05.

Results

Figure 15:
FIG. 15 shows that endothelium-dependent and -independent, NO-mediated vasodilation in Gper$^{+/+}$ and Gper$^{-/-}$ mice. Endothelium-dependent, NO-mediated vasodilation to acetylcholine (a) and endothelium-independent, NO-mediated vasodilation to sodium nitroprusside (b) in young (4 month-old) and aged (24 month-old) Gper$^{+/+}$ and Gper$^{-/-}$ mice are shown. In young mice, endothelium-dependent, NO-mediated vasodilation is fully preserved and unaffected by Gper deletion or the Nox-selective inhibitor gp91ds-tat (tat, a). Endothelium-independent, NO-mediated vasodilation is maintained in aged mice and independent of Gper. All data (n=4-8) are mean±s.e.m.
Figure 15:
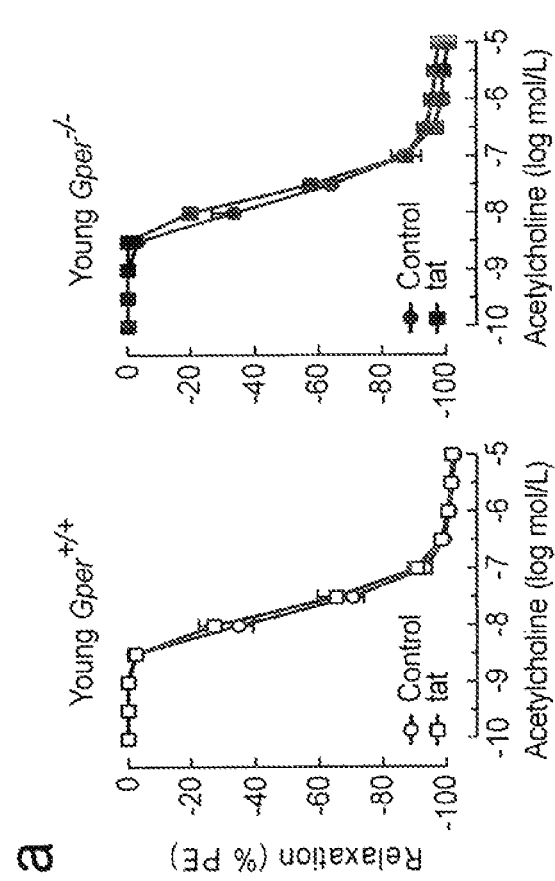

GPER Regulates Age-Dependent Vascular Dysfunction, Superoxide Production and Nox1 Expression Based on our preliminary observation that deletion of Gper abolishes Ang II-induced, Nox-mediated superoxide production in VSMC, we hypothesized that GPER might be involved in the cardiovascular aging process through regulation of Nox activity and the associated oxidative stress. Given that superoxide generation increases with aging and thereby reduces the bioavailability of endothelial nitric oxide (NO), we first investigated endothelium-dependent, NO-mediated vasodilation. In Gper$^{+/+}$ mice, aging markedly reduced endothelium-dependent relaxation to acetylcholine. This effect was completely restored by the Nox-selective inhibitor gp91ds-tat, a peptide directed against a homologous 9 amino acid sequence in the Nox1 and Nox2 catalytic subunits that prevents the interaction with p47$^{phox}$ required for activation (FIG. 10a and FIG. 15a). By contrast, Gper$^{-/-}$ mice were completely resistant to the age-dependent impairment of endothelium-dependent relaxation. Responses were comparable to that of young mice and not further affected by Nox inhibition (FIG. 15). Similarly, Nox inhibition reduced contractions to Ang II, a vasoconstrictor and prototypic inductor of vascular Nox1 activity, only in arteries of aged Gper$^{+/+}$ mice; contractions in Gper$^{-/-}$ mice were ~50% lower than in Gper$^{+/+}$ mice and also unaffected by Nox inhibition (FIG. 10b). Based on these unexpected findings, we next examined basal vascular superoxide production. We found that ~50% of vascular superoxide in Gper$^{+/+}$ mice (FIGS. 10c and 10d) is generated by Nox as it could be blocked by gp91ds-tat (FIG. 10c). By contrast, deletion of Gper was associated with a ~50% lower vascular superoxide production that was unaffected by gp91ds-tat (FIG. 10c). Consistent with lower superoxide levels in Gper$^{-/-}$ mice, vascular expression of Nox1, the main catalytic isoform in large rodent arteries, was greatly reduced by ~80% in Gper$^{-/-}$ compared to Gper$^{+/+}$ mice (FIG. 10e).

Obligatory Role of GPER for Age-Dependent Cardiac Fibrosis and Diastolic Dysfunction Having demonstrated that constitutive Gper expression is required for Nox-dependent vascular superoxide generation and since superoxide plays a central role in cardiac aging, we determined whether GPER also affects superoxide production in the aging heart. As with the vasculature, superoxide production (FIG. 10f), nitrotyrosine staining (a marker of cell injury by peroxynitrite, which is formed by the reaction of superoxide with NO, FIG. 10g) and Nox1 expression (FIG. 10h) in the left ventricle were markedly reduced in aged Gper$^{-/-}$ mice. These findings suggested that lack of Gper limits Nox-derived myocardial superoxide production and the associated tissue injury.

Figure 16:
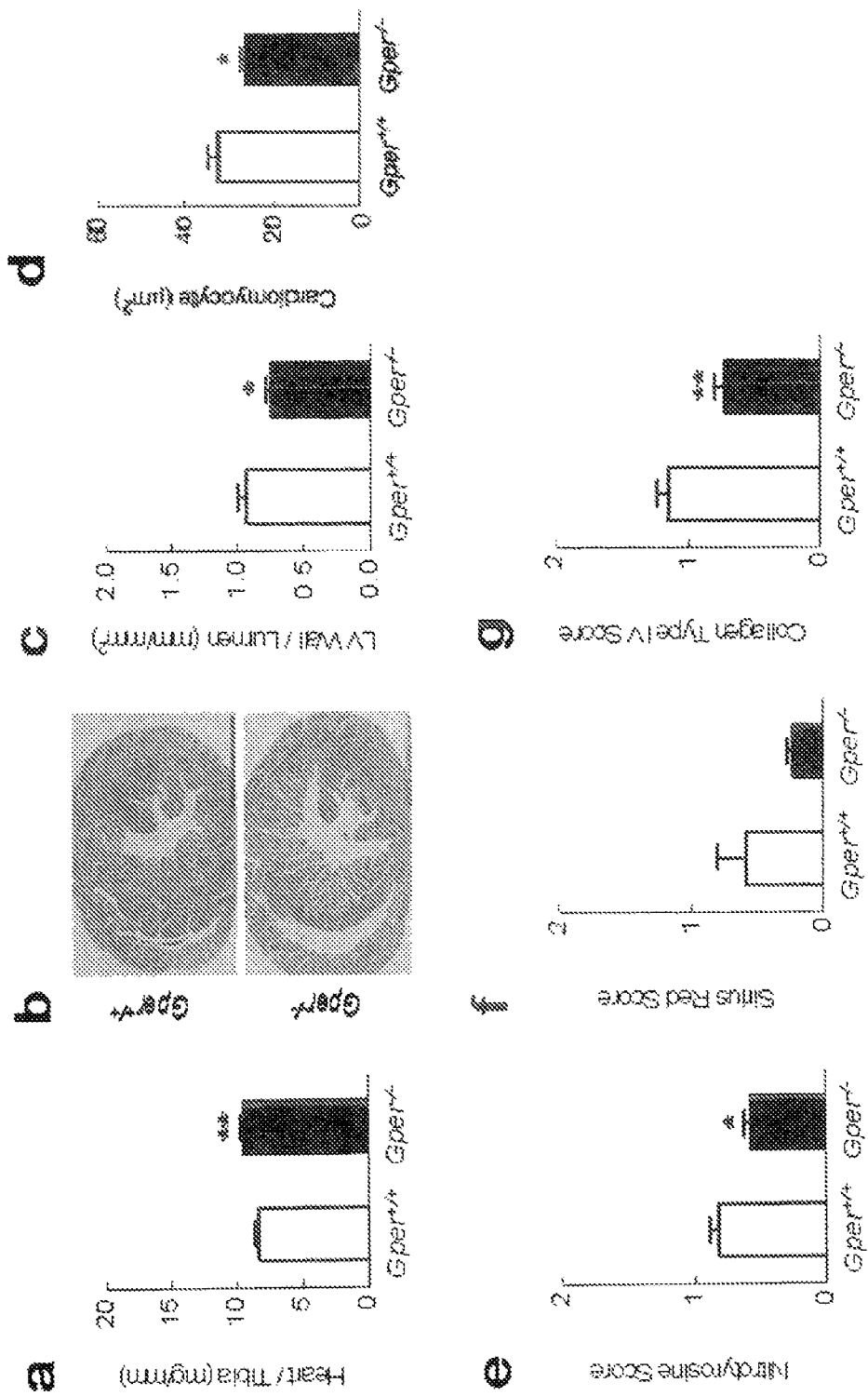
FIG. 16 shows early inhibition of myocardial oxidative stress and fibrosis by Gper deletion in adult mice. Total heart weights (a) and histologic myocardial changes (b-g) in adult (12 month-old) Gper$^{+/+}$ (open bars) and Gper$^{-/-}$ (closed bars) mice. Heart weight (relative to tibial length, a) is slightly increased in Gper$^{-/-}$ mice; however, left ventricular hypertrophy (as measured by left ventricular wall to lumen ratio in cross sections, b-c) is inhibited by Gper deficiency, as is cardiomyocyte area (d). This is associated with less oxidative stress (determined by nitrotyrosine staining, e), a tendency for inhibition of interstitial fibrosis (Sirius red staining, f), and significantly reduced collagen type IV content (g) in Gper$^{-/-}$ mice. All data (n=6-18 per group) are mean±s.e.m. *P<0.05, **P<0.01 vs. Gper$^{+/+}$ mice (Student's t-test).

To test whether the activating function of GPER on Nox-dependent superoxide production contributes to the functional and structural abnormalities associated with cardiac aging in vivo, we studied cardiac pathology and left ventricular function. In contrast to Gper$^{+/+}$ mice, Gper$^{-/-}$ mice were resistant to the development of age-dependent cardiac hypertrophy as determined by heart weight (FIG. 11a and FIG. 16) and LV morphology (FIGS. 11b ROS and 11c). Histomorphometry demonstrated increased thickness of the interventricular septum and the left-ventricular lateral wall of aged Gper$^{+/+}$ mice; again, hearts of Gper mice were resistant to these alterations (1.80.1 mm vs. 1.2±0.1 mm and 2.1±0.1 mm vs. 1.6±0.1 mm, respectively, n=6-7, each p<0.001). As a result, the LV wall-to-lumen ratio (an indicator of hypertrophy) in Gper$^{+/+}$ mice increased by 59% with aging. Cardiomyocyte size (hypertrophy) was also reduced in Gper mice (FIG. 11d). Aging in Gper$^{+/+}$ mice is characterized by marked myocardial fibrosis (FIGS. 11e and 11f) and greatly increased myocardial collagen type IV content (FIG. 11g). In contrast, myocardial fibrosis was greatly reduced in the LV of Gper$^{-/-}$ mice (FIGS. 11e and 11g), which was comparable to that of young Gper$^{+/+}$ mice (Suppl. FIGS. 11f and 11g). A trend towards the protective effect of Gper deficiency was already detectable in adult mice at 12 months of age (FIGS. 16f and 16g).

Given that Gper deletion prevented age-dependent LV hypertrophy and fibrosis, we hypothesized that this would result in differential LV function in vivo, which was studied by echocardiography. Gper$^{+/+}$ mice were normotensive (FIG. 20, Table 1) but displayed a marked increase in thickness of the inter-ventricular septum, the LV posterior wall, the relative wall thickness as well as LV mass compared with Gper$^{-/-}$ mice (FIG. 11h and FIG. 20, Table 1). Consistent with previous findings, LV ejection fraction was ~45% in aged Gper$^{-/-}$ and Gper$^{+/+}$ mice (FIG. 20, Table 1), and there were no differences in LV or RV cardiac output between groups (not shown). However, diastolic function (due to increased ventricular stiffness) measured by early diastolic mitral valve annular velocity (E', FIG. 11i) and myocardial performance index (MPI, FIG. 11j) was markedly better in aged Gper$^{-/-}$ mice. Similarly, there was a strong trend towards lower mitral inflow E/A ratio in aged Gper$^{+/+}$ mice (FIG. 20, Table 1), which correlates well with diastolic dysfunction in mice. Taken together, the lack of LV hypertrophy and fibrosis with aging in Gper$^{-/-}$ mice is associated with improved LV elasticity, as indicated by improved left-ventricular diastolic filling, changes that occur independently of systemic blood pressure.

Expression of GPER is Required for Vascular Smooth Muscle Cell Nox Activity

Having established that Gper deficiency prevents elevated, Nox-dependent cardiovascular superoxide levels in aged mice, we next determined whether stimulated Nox activity in adult mice also depends on the presence of Gper. Ang II is a potent activator of Nox in VSMC, and ROS produced in response to Ang II are involved in central redox-sensitive cell functions such as intracellular calcium mobilization and contraction. Using the Nox-selective inhibitor gp91ds-tat, we found that Ang II-mediated contractions substantially depend on Nox activity in arteries of Gper$^{+/+}$ mice. In contrast, contractions to Ang II were ~40% less potent in Gper$^{-/-}$ mice and completely resistant to Nox inhibition (FIG. 12a). KCl-induced contractions as a measure of receptor-independent vascular contractility were unaffected by Gper deficiency (not shown).

We next set out to study more detailed mechanisms in VSMC derived from Gper$^{+/+}$ and Gper$^{-/-}$ mice. Consistent with the activation of Nox in arteries expressing Gper, Ang II-stimulated superoxide production in these cells was largely inhibited by gp91ds-tat. By contrast, in cells lacking Gper, the Ang II-stimulating effect on superoxide generation was almost completely abolished (FIGS. 12b and 12c). Mobilization of intracellular calcium in response to Ang II, which is Nox-mediated, was similarly abolished in VSMCs obtained from Gper$^{-/-}$ mice (FIGS. 12d and 12e). In contrast, responses to the purinergic receptor agonist ATP, which causes Nox-independent rapid increases in intracellular calcium, were comparable in VSMC from Gper$^{+/+}$ and Gper$^{-/-}$ mice, excluding inherent alterations in calcium signaling in VSMC lacking Gper (FIG. 12f). These findings confirm that VSMC contraction, superoxide production and calcium mobilization in response to Ang II are mediated by Nox,[6] and demonstrate for the first time an obligatory role for GPER as a newly identified activator of Ang II-stimulated Nox activity and the associated ROS-dependent cell functions.

GPER Regulates Vascular Nox1 Expression and Activity

Figure 17:
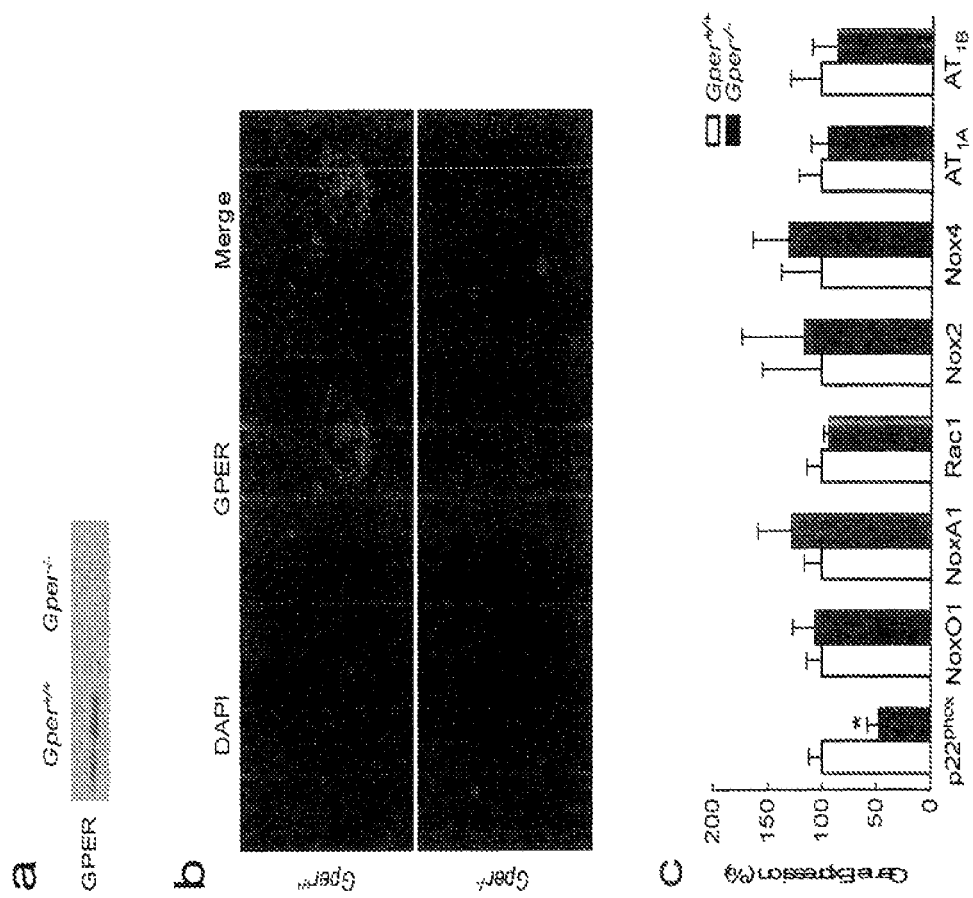
FIG. 17 shows that role of GPER for expression of NADPH oxidase subunits in vascular smooth muscle cells. GPER protein expression detected by Western blot (a) and immunofluorescence (green, b), as well as gene expression of the adaptor proteins p22$^{phox}$ and NoxO1, of the activator proteins NoxA1 and Rac1, of the catalytic subunits Nox2 and Nox4, and of the Ang II receptors AT$_{1A}$ and AT$_{1B}$ in vascular smooth muscle cells isolated from Gper$^{+/+}$ (open bars) and Gper$^{-/-}$ (closed bars) mice. GPER protein expression was verified in cells isolated from Gper$^{+/+}$ mice (a-b). The nucleus was stained with DAPI (blue, b). Gper deletion reduced p22$^{phox}$ gene expression, but had no effect on expression of other NADPH oxidase subunits or AT$_1$ receptors. All data (n=4-8 per group) are mean±s.e.m. *P<0.05 vs. Gper$^{+/+}$ mice (Student's t-test). (c) shows the gene expression of a number of Nox isoforms and activator and adaptor proteins.
Figure 18:
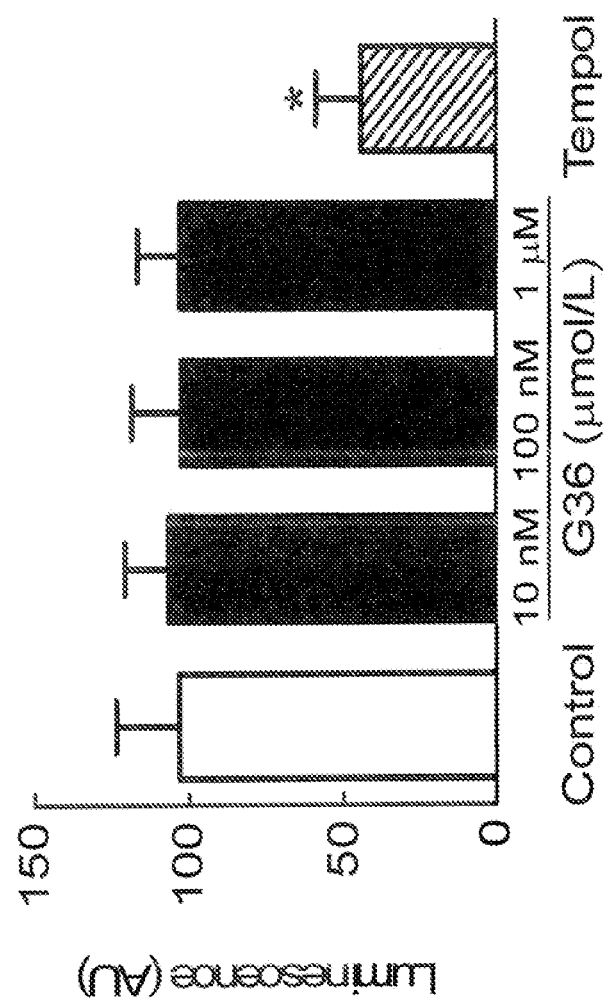
FIG. 18 shows the role of the GPER-selective antagonist G36 on superoxide-production in a cell-free assay. Effects of G36 (0.01, 0.1 and 1 mmol/L) compared to control (DMSO 0.01%) and the superoxide dismutase mimetic tempol (100 mmol/L) on superoxide generation by xanthine oxidase were determined by chemiluminescence. G36 displays no antioxidant activity. All data (n=4-5 per group) are mean±s.e.m. *P<0.05 vs. control (Student's t-test).
Figure 19:
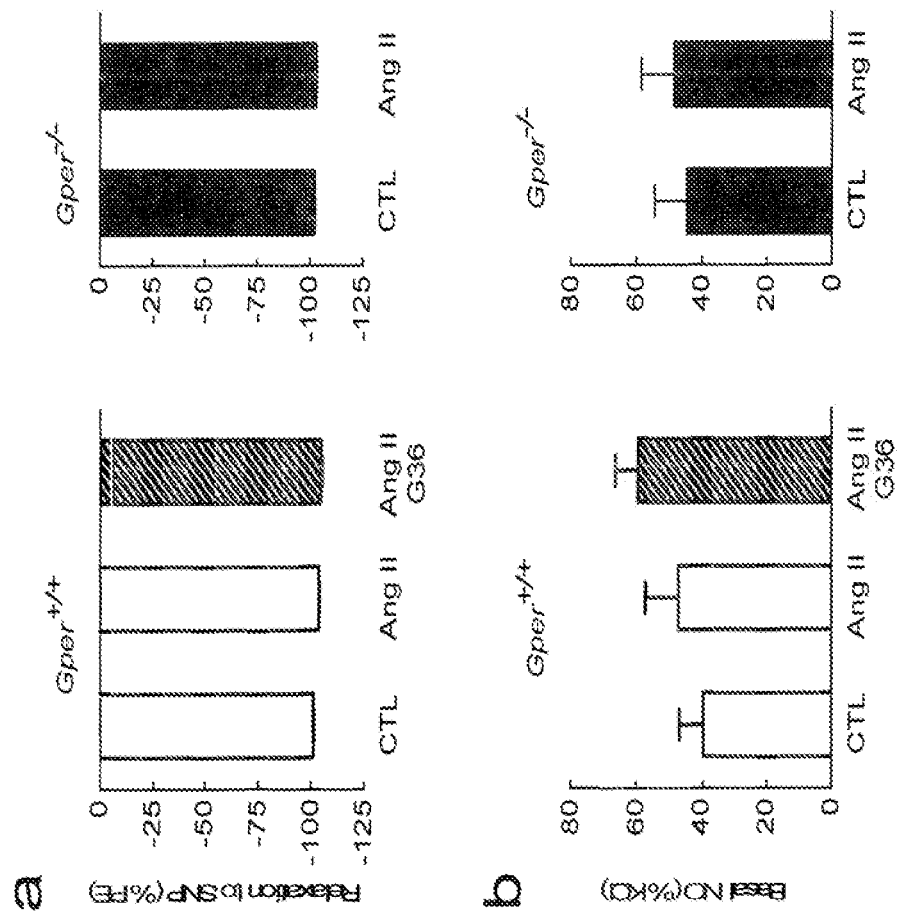
FIG. 19 shows the role of GPER inhibition on vascular NO sensitivity and basal NO bioactivity in Ang II-induced hypertension. Gper$^{+/+}$ (open bars) and Gper$^{-/-}$ (closed bars) mice were infused with Ang II (0.7 mg/kg per day) or vehicle (control, CTL) for 14 days. A subset of Gper$^{+/+}$ mice was also treated with the GPER-selective antagonist G36 (hatched bars). Vasodilation to the NO donor sodium nitroprusside (SNP, a) and basal vascular NO bioactivity (b) are shown. Neither Gper deletion nor inhibition of GPER by the selective antagonist G36 had an effect on NO sensitivity (a) or basal NO bioactivity (b). All data (n=4-10 per group) are mean±s.e.m.

Nox1 is the primary superoxide-generating Nox subunit in vascular smooth muscle of large arteries and mediates Ang II-induced increases in vascular tone. Consistent with the complete lack of Ang II-stimulated Nox activity in Gper-deficient VSMC (FIG. 12), steady-state Nox1 gene and protein expression was greatly reduced in Gper-deficient VSMCs compared with cells isolated from Gper$^{+/+}$ mice (by ~70% each, FIGS. 13a and 13b). mRNA levels of the transmembrane scaffolding subunit p22$^{phox}$ were also reduced in VSMC from Gper$^{-/-}$ mice, while expression of other Nox isoforms, adaptor and activator proteins was unaffected (FIG. 17). To verify whether the down-regulation of Nox1 expression is responsible for the inability of VSMC lacking Gper to increase superoxide production in response to Ang II, we restored Nox1 protein levels in these cells utilizing an adenovirus system (AdNox1). Reintroducing Nox1 into Gper-deficient cells completely recovered the capability to generate superoxide in response to Ang II (FIG. 13c).

To corroborate these findings, we next studied Nox activity and expression in human VSMC. We found that knockdown of GPER similarly abolished the cellular ability to increase superoxide production in response to Ang II (FIG. 13d), further underscoring the functional interdependence between GPER and Nox1. Consequently, we employed the synthetic, small molecule, GPER-selective antagonist G36 to determine whether pharmacological inhibition of GPER can recapitulate such effects. Importantly, G36 displays no direct antioxidant activity (FIG. 17). We found that the Nox-selective inhibitor gp91ds-tat, but not acute treatment with G36 (for 30 min) abolished Ang II-stimulated superoxide production (FIG. 13e). In contrast, prolonged treatment with G36 (for 72 hours) fully abolished the generation of superoxide in response to Ang II, suggesting a genomic, GPER-mediated mechanism (FIG. 13e). Consistently, long-term G36 treatment also reduced Nox1 expression in VSMC (FIG. 13f). In conclusion, we identified GPER as a novel activator of Nox1 gene and protein expression and found that G36 acts as a viable pharmacologic inhibitor of Nox1 expression and activity in human VSMC.

Pressor Effects of Ang II Require Constitutive GPER Expression

Figure 13:
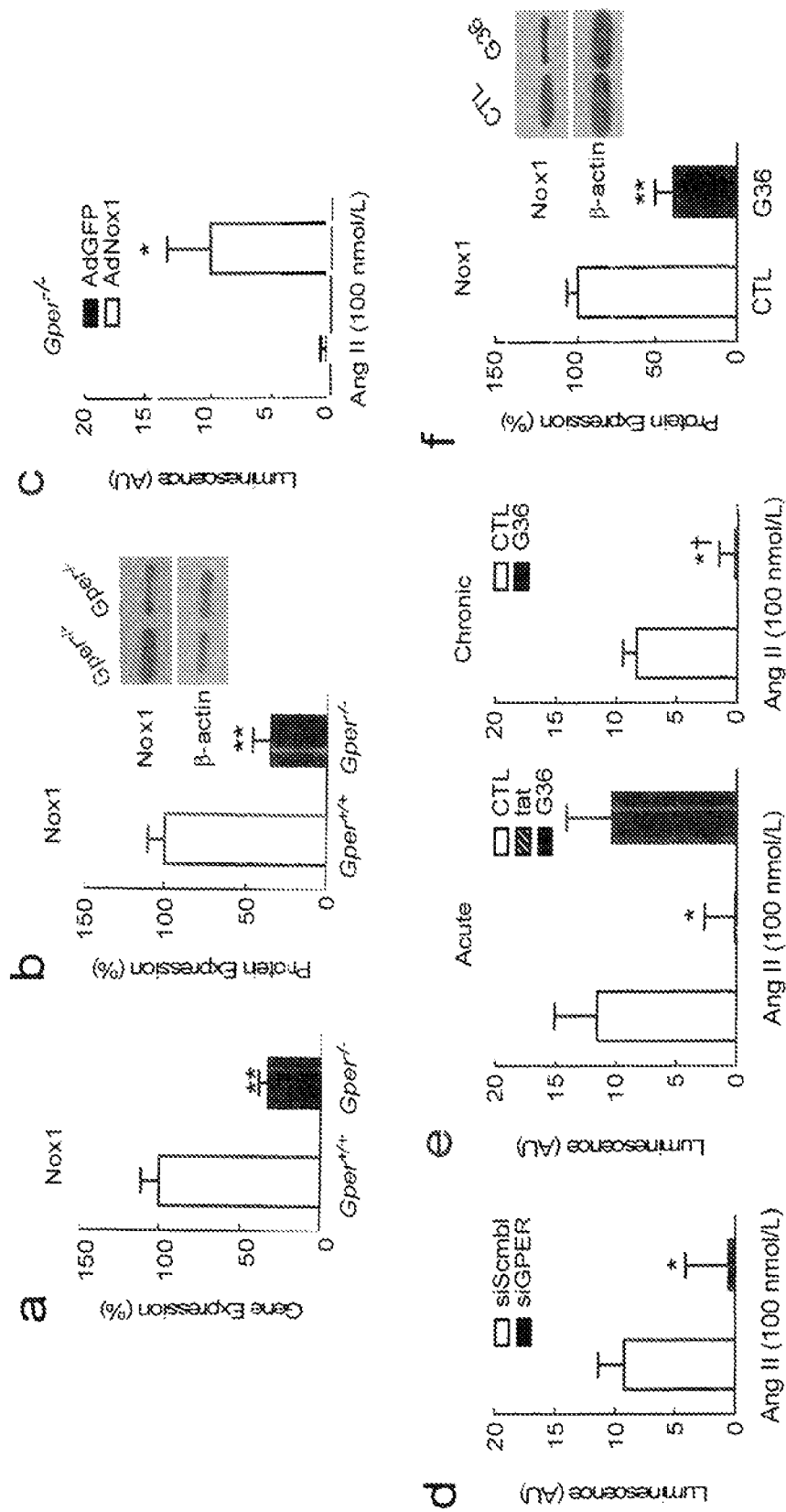
FIG. 13 shows that GPER regulates Nox1 expression and activity in murine and human vascular smooth muscle cells. Nox1 gene (a) and protein expression (b, f), and superoxide production detected by chemiluminescence (c-e) in VSMC isolated from Gper$^{+/+}$ (open bars) and Gper$^{-/-}$ (closed bars) mice (a-c) and in human VSMC (d-f). Deletion of Gper$^{+/+}$ markedly reduces gene and protein expression of Nox1 in murine VSMC (a-b; **P<0.01 vs. Gper$^{+/+}$, Student's t-test). Transfection of VSMC with Nox1-containing adenovirus (AdNox1) completely restores Ang II-dependent superoxide production in Gper$^{-/-}$ cells compared to cells transduced with vector control (AdGFP, c; *P<0.05 vs. AdGFP, Student's t-test). Similarly, GPER-targeted gene silencing (siG-PER), using scrambled siRNA (siScmbl) as control, completely abrogated Ang II-induced superoxide production in human VSMC (d; *P<0.05 vs. siScmbl, Student's t-test). Regulation of Nox1 through GPER requires genomic effects as acute (30 min) treatment of cells with the Nox-selective inhibitor gp91 ds-tat (tat, 3 mmol/L), but not with the GPER-selective antagonist G36 (100 nmol/L), fully prevented Ang II-stimulated superoxide generation (e, left panel). By contrast, in cells treated with G36 for 72 hours, superoxide production was abrogated (e, right panel) and Nox1 expression (f) greatly reduced. *P<0.05, **P<0.01 vs. control (CTL, DMSO 0.01%); †P<0.05 vs. acute treatment (ANOVA with Bonferroni post-hoc tests in e; Student's t-test in f). All data (n=4-9) are mean±s.e.m.
Figure 14:
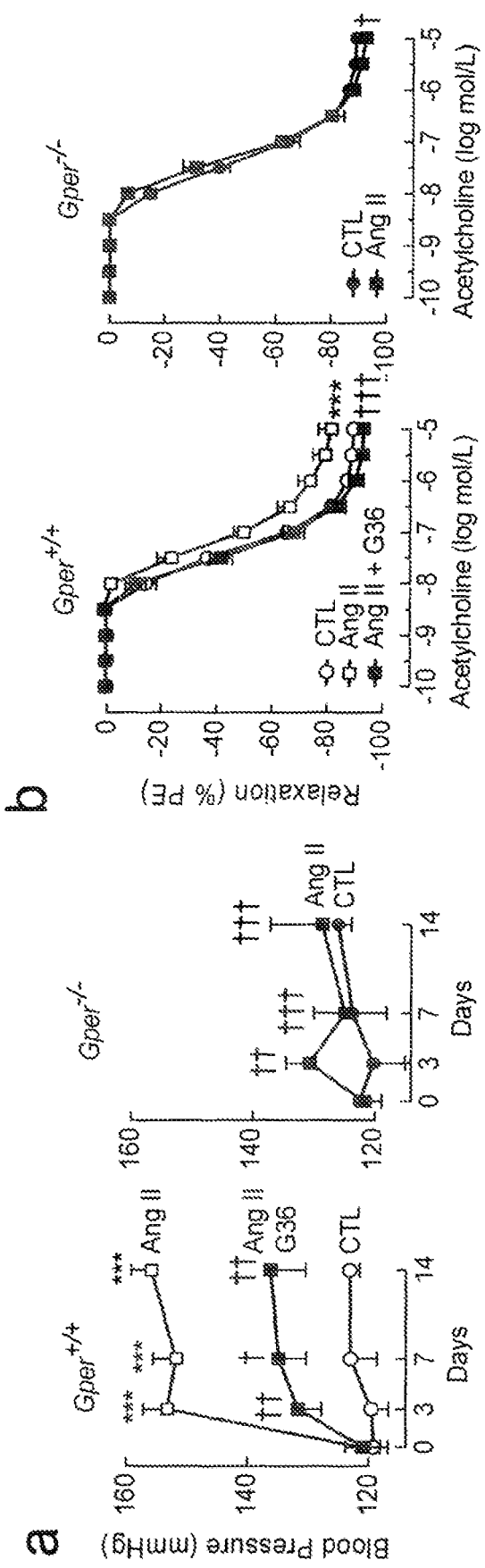
FIG. 14 that inhibition of GPER prevents Ang II-induced hypertension, vascular dysfunction and oxidative stress in vivo. Gper$^{+/+}$ and Gper$^{-/-}$ mice were infused with Ang II (0.7 mg/kg per day) or vehicle (control, CTL) for 14 days. A subset of Gper$^{+/+}$ mice was also treated with the GPER-selective antagonist G36. Arterial blood pressure (a), endothelium-dependent, NO-mediated vasodilation to acetylcholine (b), vascular superoxide generation determined by DHE staining (c) and chemiluminescence (d), and vascular Nox1 protein immunofluorescence (e-f) are shown. In contrast to Gper$^{+/+}$ mice, mice lacking Gper are resistant to developing Ang II-induced hypertension (a) and vascular dysfunction (b). Similarly, unlike in Gper$^{+/+}$ mice, Ang II did not increase superoxide production (c-d) or Nox1 protein expression (e-f) in mice lacking Gper. In Gper$^{+/+}$ mice, treatment with the GPER-selective antagonist G36 treatment concomitant with chronic Ang II infusion markedly reduced hypertension (a), and completely normalized Ang II-induced vascular dysfunction (b), superoxide production (c-d), and Nox1 expression (e-f). All data (n=3-9) are mean± s.e.m. *P<0.05, P<0.01, *P<0.001 vs. genotype-matched CTL; †P<0.05, ††P<0.01, †††P<0.001 vs. Ang II-treated Gper$^{+/+}$ mice (ANOVA with Bonferroni post-hoc tests).
Figure 14:
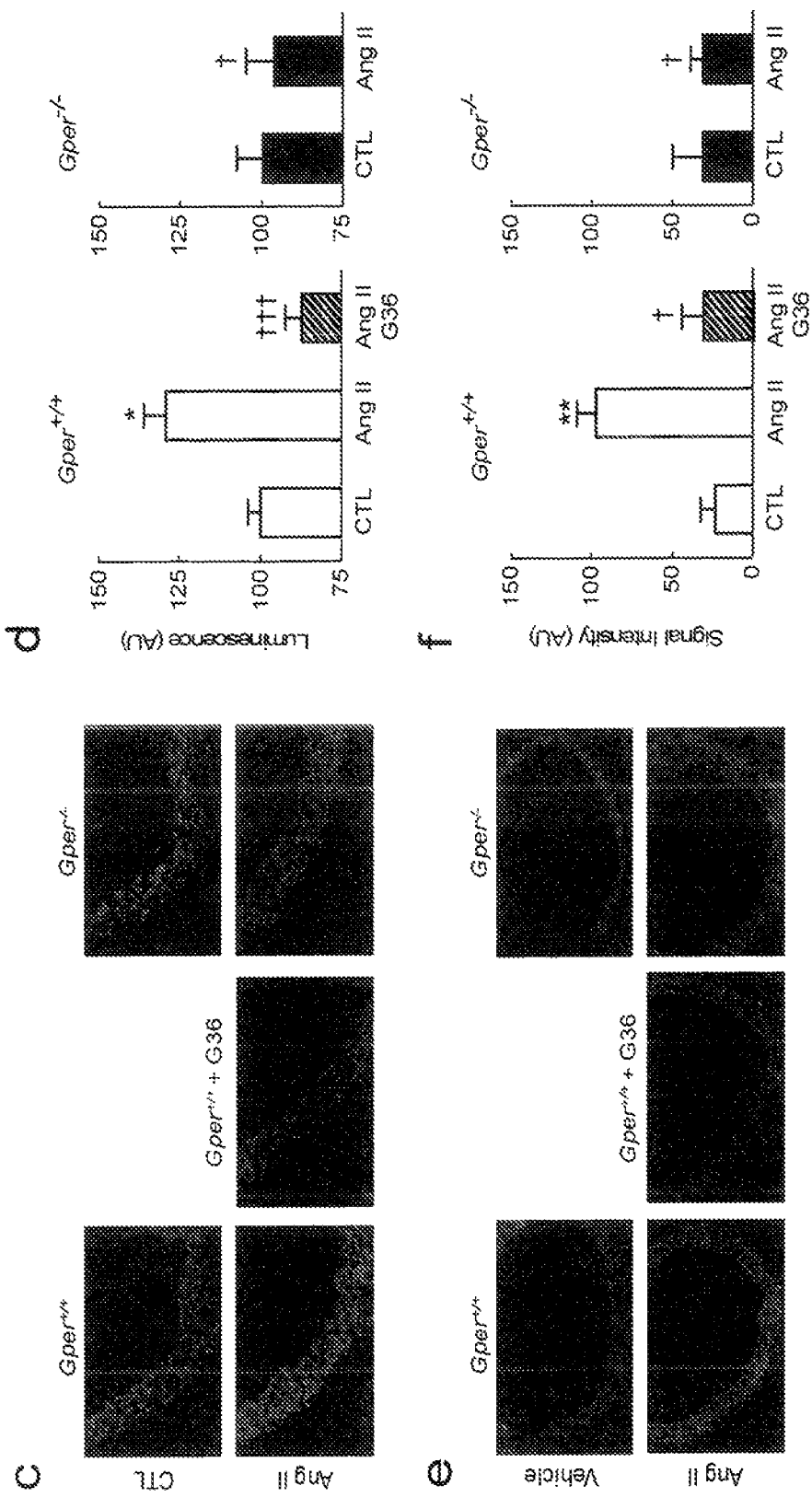

Having established a physiological role of endogenous GPER for Nox1-dependent vascular function, we next studied whether GPER contributes to arterial hypertension using the Ang II infusion model. Importantly, sustained Ang II-induced blood pressure increases require the presence of functional Nox1, which we demonstrated here depends on the activity of GPER (FIG. 13). Unlike Gper$^{+/+}$ mice, animals lacking Gper were largely resistant to the development of Ang II-induced hypertension (FIG. 14a). Since superoxide generated in response to Ang II reduces endothelial NO bioactivity and thus increases vascular tone, which can both predispose to or be a consequence of arterial hypertension, we next assessed effects of Ang II on endothelium-dependent, NO-mediated vasodilation. While Ang II-induced hypertension impaired vasodilation in Gper$^{+/+}$ mice, arteries of Gper-deficient mice were completely resistant to develop abnormal vascular function (FIG. 14b). Furthermore, increased vascular superoxide production in mice with Ang II-induced hypertension was strictly dependent on the presence of Gper (FIGS. 14c and 14d). Chronic infusion of Ang II also increased vascular Nox1 expression in Gper[+/+] mice, whereas Nox1 expression in Gper[-/-] mice was resistant to Ang II (FIGS. 14e and 14f). Thus, we identified Gper to play a critical role for Ang II-induced hypertension through activation of Nox1-mediated superoxide production and the associated impairment of endothelial cell function.

Treatment of Ang II-Induced Hypertension with a Small Molecule GPER Antagonist

Having demonstrated that endogenous GPER facilitates Nox-mediated vascular responses stimulated by Ang II, we hypothesized that treatment with a highly selective GPER antagonist, the synthetic small molecule G36, would inhibit Ang II-induced hypertension and the associated vascular oxidative stress and impairment of vascular function. Treatment with G36 substantially attenuated Ang II-induced hypertension (FIG. 14a), which was associated with preservation of endothelium-dependent, NO-mediated vasodilation (FIG. 14b). Furthermore, G36 treatment reduced vascular superoxide production (FIGS. 14c and 14d) and fully prevented the Ang II-stimulated induction of vascular expression of Nox1 (FIGS. 14e and 14f). These findings suggest that the GPER-selective antagonist G36 may serve as a novel therapeutic approach to treat Nox-dependent forms of arterial hypertension and the functional injury associated with it.

3. GPER Deficiency Protects from Age-related Chronic Kidney Disease and Dysfunction Introduction Aging is associated with reduced vasodilatory capacity in renal arteries. Activation of the G protein-coupled estrogen receptor (GPER) induces vasodilation and improves hypertensive renal injury in rats. GPER, as observed with many G protein-coupled receptors, likely exhibits "basal activity"-independent of ovarian estrogen production, which may become relevant in disease-like states such as aging. We hypothesized that deletion of basal GPER activity would further aggravate vasodilatory dysfunction in renal arteries and the glomerular and tubulointerstitial injury associated with it but unexpectedly found the opposite to be true.

Methods

In young (4 month-old) and aged (24 month-old) male wild-type and GPER-deficient (Gper-/-) mice, blood pressure was determined noninvasively using a tail-cuff volume-pressure recording system. Renal arteries were prepared for isometric force measurement in a Mulvany-Halpern myograph to study endothelium-dependent vasodilation to acetylcholine. Vasodilatation is expressed as the percentage of precontraction to phenylephrine (PE). Histological sections of paraformaldehyde-fixed kidneys were stained with Periodic-acid Schiff (PAS) for semiquantitative morphometry, and vascular injury (VIS score) and tubulointerstitial injury (TIS score) were determined. In addition, sections were stained with Congo red as a marker of collagen fibers, cytoskeletal proteins, and amyloid fibrils.

Results

Figure 22:
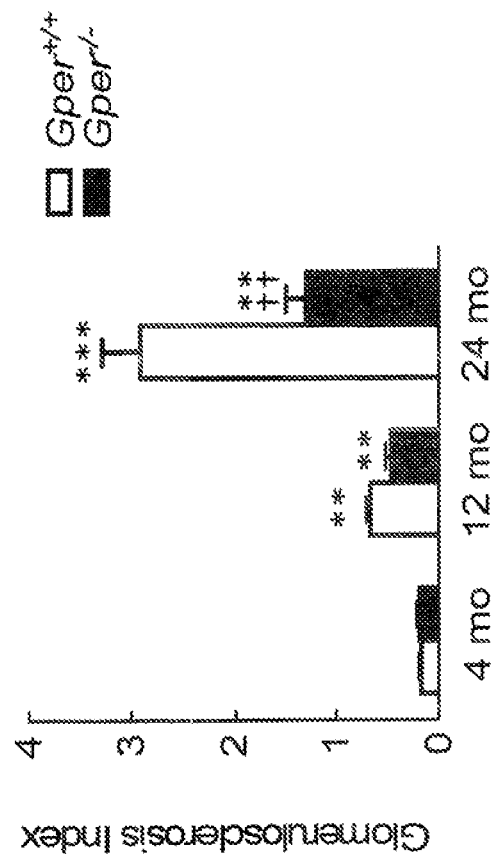
Figure 23:
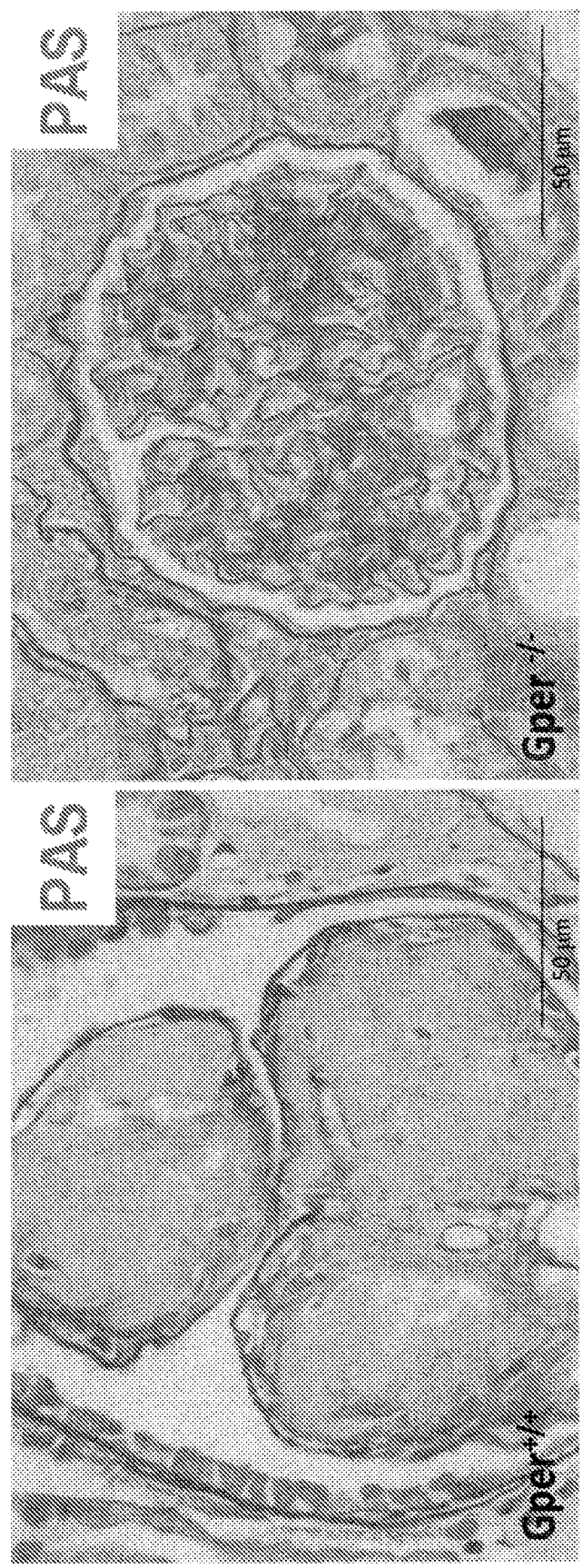
Figure 24:
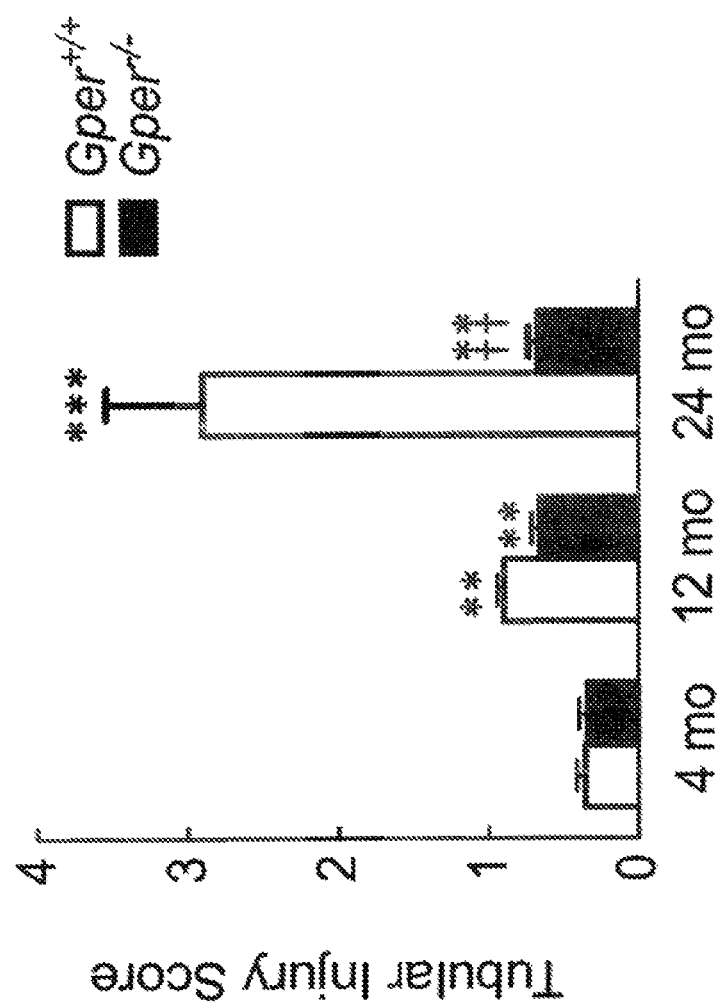
Figure 25:
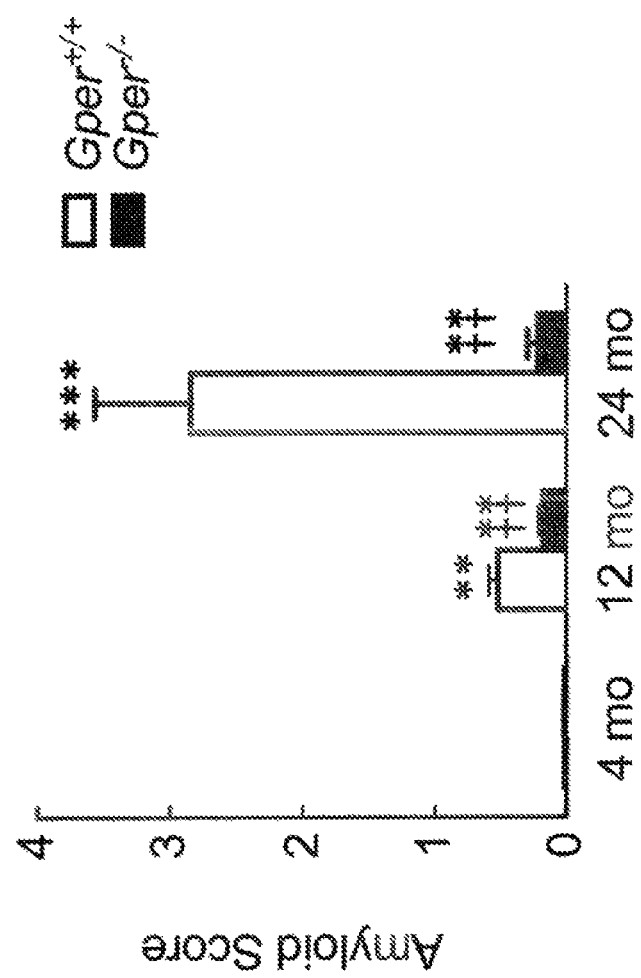
Figure 26:
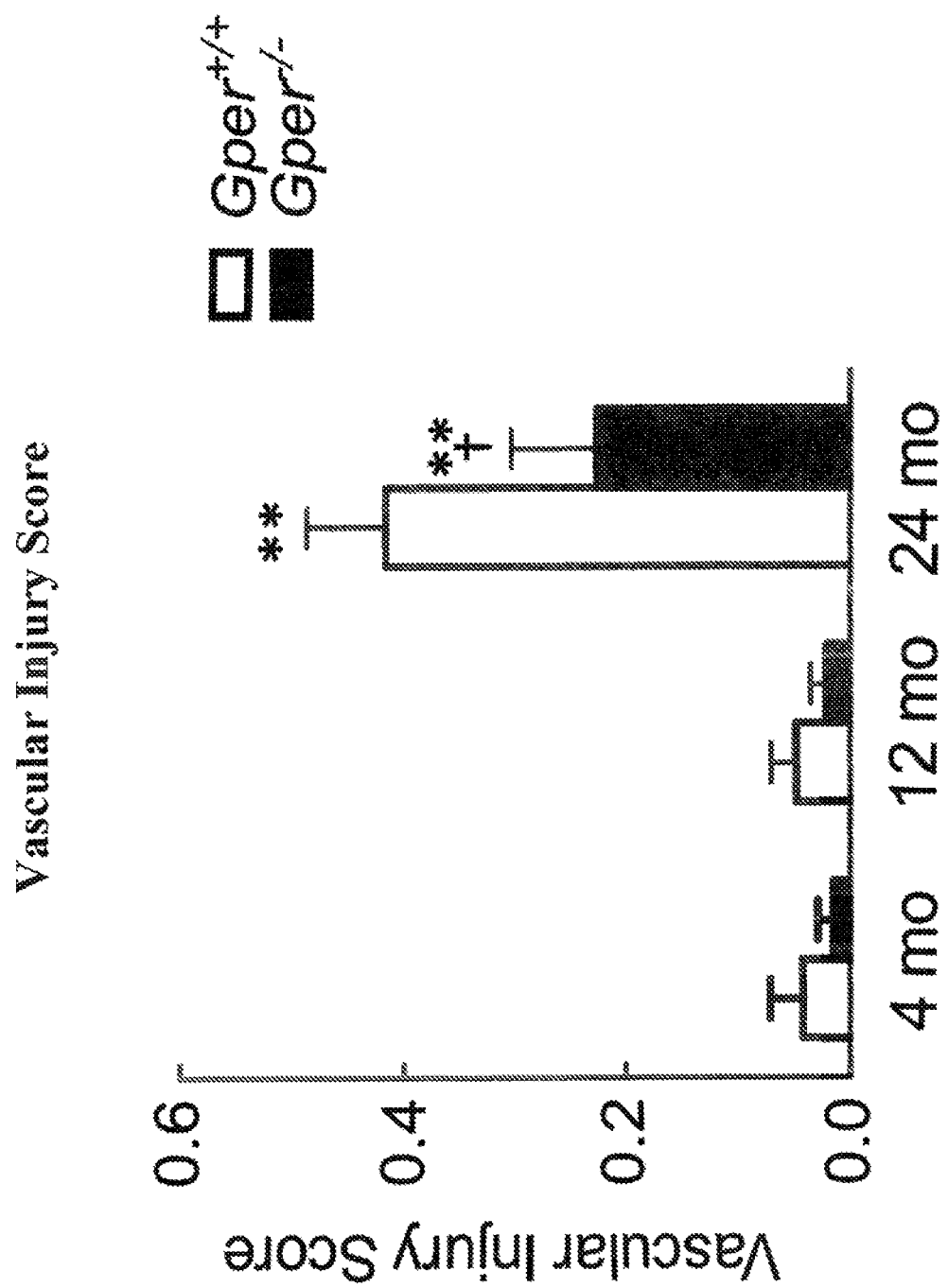
Figure 27:
Figure 29:
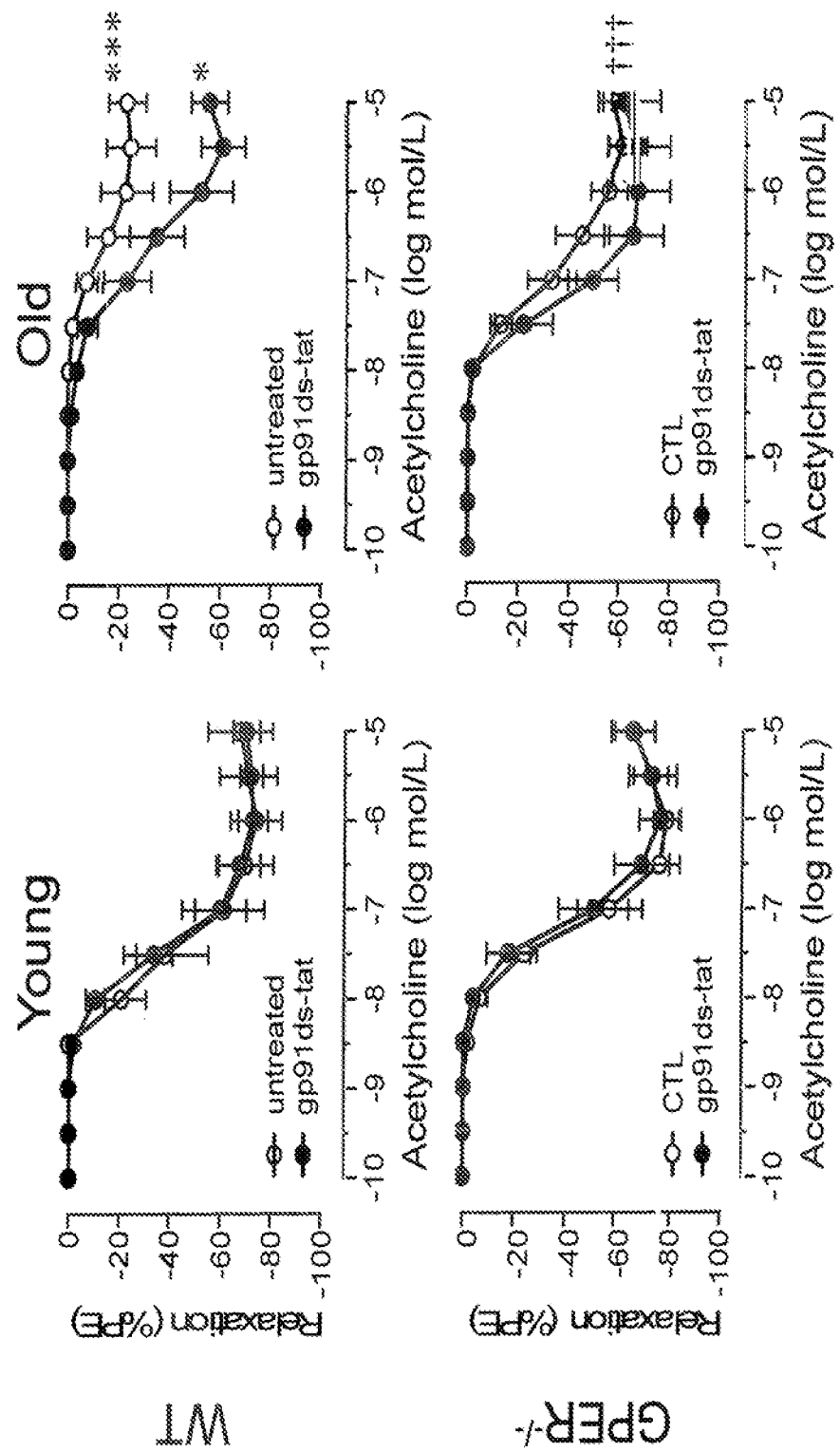
Figure 30:
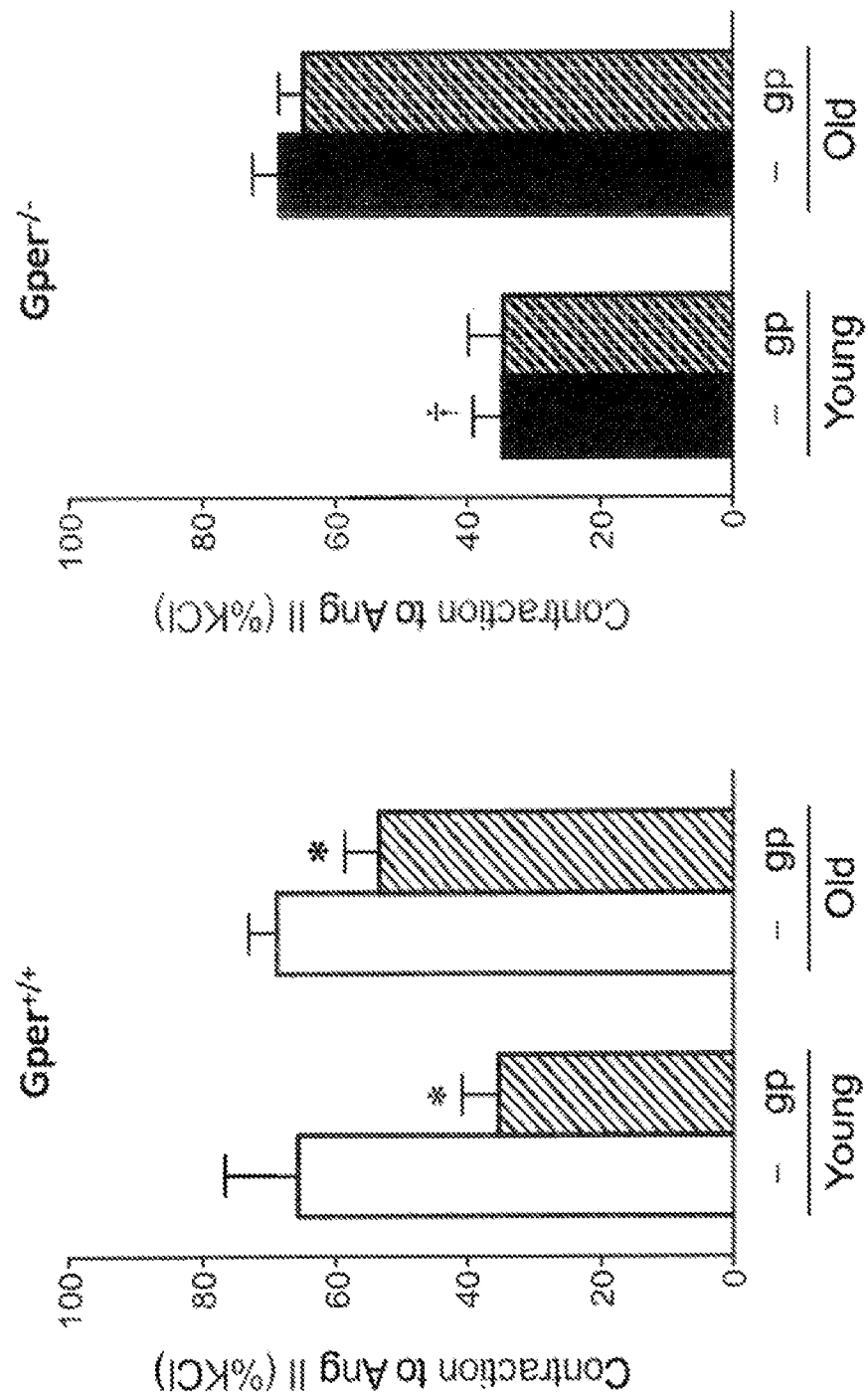

Contrary to our hypothesis and quite unexpectedly, age-dependent increases in kidney disease/dysfunction were largely absent in aged Gper-/- mice. These results are shown in attached FIG. 21-29. Deletion of Gper greatly attenuates age-dependent increases in kidney weight (FIG. 21), glomerulosclerosis (FIG. 22 ROS and FIG. 23), tubulointerstitial injury (FIG. 24), structure renal damage (amyloidosis, FIG. 25), vascular injury (FIG. 26) and proteinuria (FIG. 27), with no accompanying changes in blood pressure (FIG. 28). In aged wild type mice, vascular relaxation in response to acetylcholine is significantly reduced compared to young wild type mice; however, this deficit is largely absent in Gper-deficient mice (FIG. 29). In aged wild type mice, vascular contraction in response to angiotensin is significantly increased compared to Gper deficient mice (FIG. 30). Furthermore the fractional contraction in both young (~50%) and old (~20%) wild type mice that is due to ROS (as assessed by addition of gp91ds-tat) is absent in young and old Gper deficient mice (FIG. 30).

SUMMARY AND CONCLUSIONS

These results indicate a novel role for GPER expression and in particular, GPER inhibition in age-related impaired vasodilatory capacity in renal arteries and the associated tubulo-interstitial injury, effects that occur independent of blood pressure. These data may seem counterintuitive when compared to the current body of evidence suggesting a protective role of GPER agonists that activate rapid signaling pathways. In contrast, the present results identify new chronic functions of "basal" GPER activity in aging that may be linked to yet unidentified downstream effectors, possibly independent of endogenous estrogen. Unraveling such mechanisms may help to understand the pathophysiological role of GPER activity in age-dependent vascular and renal injury, further demonstrating the novel therapeutic approaches according to the present invention.

It is to be understood that the particular examples, materials, amounts, and procedures are to be interpreted broadly in accordance with the scope and spirit of the invention as set forth herein.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

The invention claimed is:

1. A method of treating insulin resistance in a patient or subject in need comprising administering to said patient or subject an effective amount of a compound according to the chemical structure:

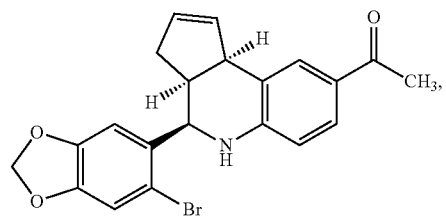

or a pharmaceutically acceptable salt thereof or a mixture thereof.

2. A method of treating insulin resistance in a patient or subject in need comprising administering to said patient or subject an effective amount of a compound according to the chemical structure:

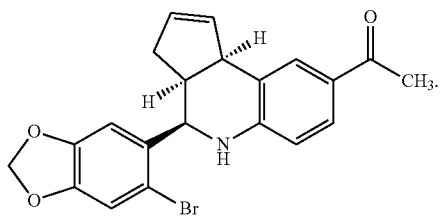 [SMILES: CC(=O)c1ccc2c(c1)[C@@H]1C=CC[C@@H]1[C@H](c1cc3c(cc1Br)OCO3)N2]
3. A method of treating insulin resistance in a patient or subject in need comprising administering to said patient or subject an effective amount of a pharmaceutically acceptable salt of the compound according to the chemical structure:
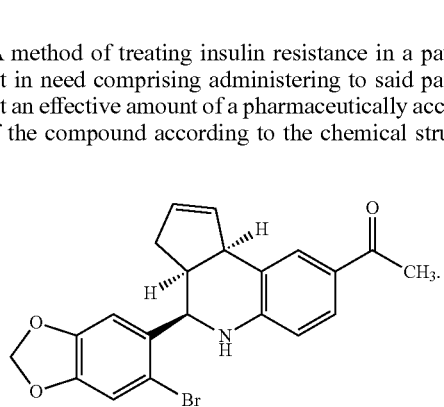
* * * * *

UNITED STATES PATENT AND TRADEMARK OFFICE
CERTIFICATE OF CORRECTION

PATENT NO. : 10,980,785 B2
APPLICATION NO. : 16/577661
DATED : April 20, 2021
INVENTOR(S) : Eric R. Prossnitz and Geetanjali Sharma It is certified that error appears in the above-identified patent and that said Letters Patent is hereby corrected as shown below:

On the Title Page

Item (72):
Remove the inventors Matthias Barton, Zurich, (CH) & Matthias R. Meyer, Stallikon, (CH)

Signed and Sealed this
Twenty-ninth Day of October, 2024

*Katherine Kelly Vidal*

Katherine Kelly Vidal
*Director of the United States Patent and Trademark Office*